(12) United States Patent
Short

(10) Patent No.: US 8,476,011 B1
(45) Date of Patent: **\*Jul. 2, 2013**

(54) CONSTRUCTION AND USE OF CATALOGUED NUCLEIC ACID LIBRARIES THAT CONTAIN ADVANTAGEOUSLY ADJUSTED REPRESENTATIONS OF DEFINED COMPONENTS

(75) Inventor: Jay M. Short, Encinitas, CA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/089,789

(22) Filed: Jun. 3, 1998

Related U.S. Application Data

(63) Continuation-in-part of application No. 09/034,724, filed on Mar. 4, 1998, now Pat. No. 6,001,574, which is a continuation-in-part of application No. 08/665,565, filed on Jun. 18, 1996, now Pat. No. 5,763,239.

(51) Int. Cl.
| | |
|---|---|
| *C12Q 1/68* | (2006.01) |
| *C07H 21/02* | (2006.01) |
| *C07H 21/04* | (2006.01) |
| *C12N 5/00* | (2006.01) |

(52) U.S. Cl.
USPC .............. 435/6.1; 435/5; 435/7.1; 435/320.1; 435/91.1; 536/23.1

(58) Field of Classification Search
USPC .......................... 435/6, 320.1, 91.1; 536/23.1
See application file for complete search history.

(56) References Cited

FOREIGN PATENT DOCUMENTS

| WO | 95/08647 | 3/1995 |
|---|---|---|
| WO | WO 95 08647 | 3/1995 |
| WO | 97/48717 | 12/1997 |
| WO | WO 97/48717 | 12/1997 |
| WO | WO 99/15702 | 4/1999 |
| WO | WO 99/45154 | 9/1999 |

OTHER PUBLICATIONS

Simoens et al., "Isolation of genes expressed in specific tissues of *Arabidopsis thaliana* by differential screening of a genomic library," *Gene*, 67:1-11 (1988).
Patanjali et al., "Construction of a uniform-abundance (normalized) cDNA library," *Proc. Natl. Acad. Sci. USA* 88:1943-1947 (Mar. 1991).
Soares et al., "Construction and characterization of a normalized cDNA library," *Proc. Natl. Acad. Sci. USA* 91:9228-9232 (Sep. 1994).
Stein et al., "Characterization of Uncultivated Prokaryotes: Isolation and Analysis of a 40-Kilobase-Pair Genome Fragment from a Planktonic Marine Archaeon," *Journal of Bacteriology* 178(3):591-599 (Feb. 1996).

*Primary Examiner* — Sean McGarry
(74) *Attorney, Agent, or Firm* — Michael F. Kolman

(57) ABSTRACT

A process for constructing a catalogued nucleic acid library in which the proportional representation of the constituents is adjusted to advantage through the use of disclosed technologies for positive and negative selection. The resultant benefit is that significantly fewer library constituents will need to be screened in order to identify a potentially desired constituent. Moreover, library constituents that previously would have been essentially "lost" are now recoverable. Preferred embodiments of this invention include the cataloguing, normalization, and enrichment of library constituents. By way of example, but not limitation, this technology is serviceable for constructing a library that contains an adequate representation of desirable constituents that (1) are initially found in low-copy numbers within a sample source or (2) originate from an organism that is problematic to culture. Applicable uses of this invention include any library-screening endeavor previously hindered by logistical impediments.

By expanding previous logistical frontiers this invention allows for a novel generation of previously unattainable molecules—particularly molecules that are "unclonable" from conventional, unadjusted libraries—to now be detected, cloned, manipulated, expressed, studied, and used. By disclosing the construction and screening of high yielding nucleic acid libraries from mixed and uncultivated organisms, the instant technology eclipses former boundaries in the area of biological discovery and enables the full breadth of biological diversity to be accessed in the search for previously undiscovered genes and gene products. The benefits of the present invention are seen to extend to areas of diagnosis, medicine, agriculture, manufacturing, and academia.

48 Claims, 2 Drawing Sheets

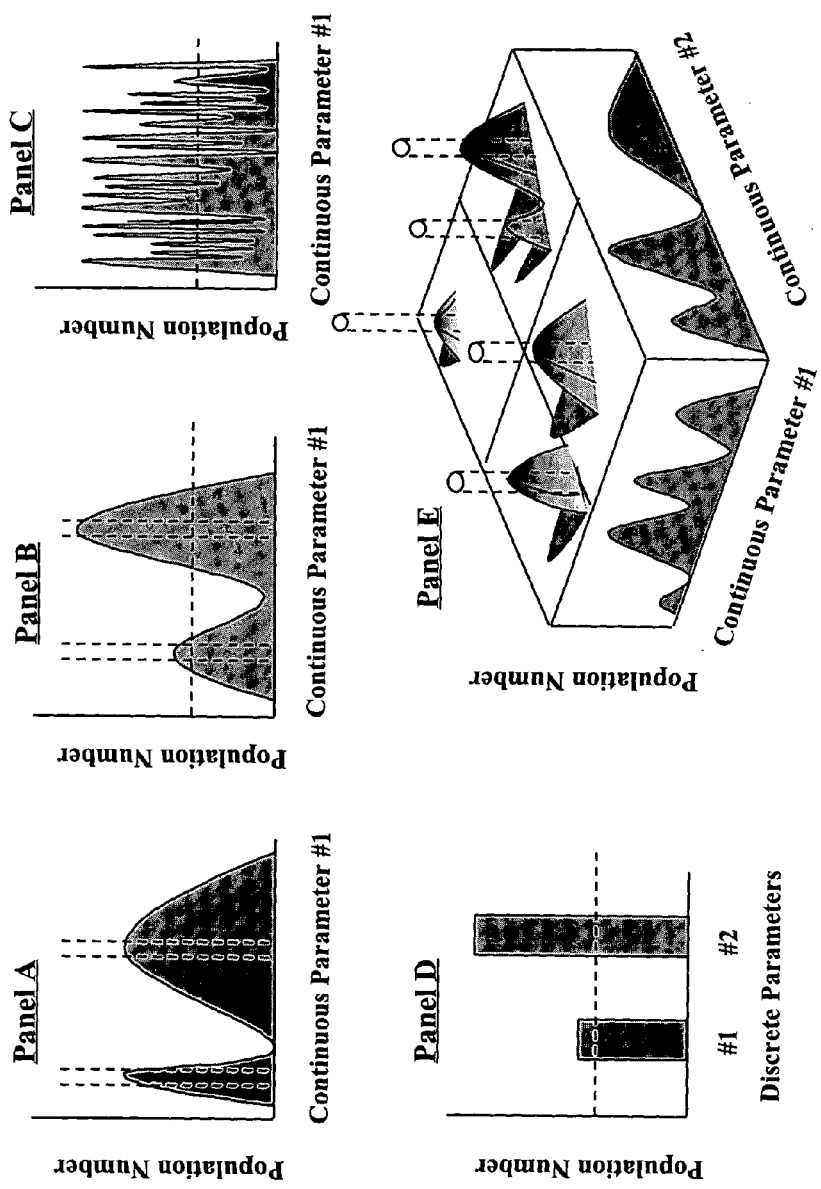

Figure 2. The proportional representation of a plurality of components in a working sample may be advantageously adjusted according to one or more parameters. In a particularly preferred but non-limiting aspect, recovery limits (dashed lined) are applied to achieve either a normalized sample or alternatively a sample in which targeted components are selectively enriched.

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
agagtttgat cctggctcag         20

<210> SEQ ID NO 2
<211> LENGTH: 19
<212> TYPE: DNA
<213> ORGANISM: Artificial Sequence
<220> FEATURE:
<223> OTHER INFORMATION: PCR Primer

<400> SEQUENCE: 2
ggttaccttg ttacgactt          19

<210> SEQ ID NO 3
<211> LENGTH: 38
<212> TYPE: DNA
<213> ORGANISM: Artificial Sequence
<220> FEATURE:
<223> OTHER INFORMATION: PCR Primer

<400> SEQUENCE: 3
gcggatccgc ggccgctgca cayctggtyg atyctgcc          38

<210> SEQ ID NO 4
<211> LENGTH: 17
<212> TYPE: DNA
<213> ORGANISM: Artificial Sequence
<220> FEATURE:
<223> OTHER INFORMATION: PCR Primer

<400> SEQUENCE: 4
gacgggcggt gtgtrca            17

CONSTRUCTION AND USE OF CATALOGUED NUCLEIC ACID LIBRARIES THAT CONTAIN ADVANTAGEOUSLY ADJUSTED REPRESENTATIONS OF DEFINED COMPONENTS

This application is a continuation-in-part of U.S. patent application entitled "Production and Use of Normalized DNA Libraries", Ser. No. 09/034,724, filed Mar. 4, 1998 now U.S. Pat. No. 6,001,574; which is a continuation-in-part of U.S. patent application entitled "Production and Use of Normalized DNA Libraries", Ser. No. 08/665,565, filed Jun. 18, 1996 now U.S. Pat. No. 5,763,239.

FIELD OF THE INVENTION

The present invention relates to the production and screening of nucleic acid libraries, and more particularly to the production and screening of nucleic acid libraries from mixed populations of prokaryotes, eukaryotes, and/or other organisms wherein the proportional representations of defined components of the libraries are adjusted to advantage. Preferred advantageous adjustments include the normalization and the selective enrichment of library components.

BACKGROUND OF THE INVENTION

The General Problem to be Solved:

In sum, it is often desirable but logistically unfeasible to isolate a nucleic acid from a library because the desired nucleic acid is too severely underrepresented.

This problem arises in the screening of a nucleic acid library constructed from a plurality of heterogeneous organism forms, particularly when a desirable source organism form is disproportionately underrepresented. This problem additionally arises when a desired nucleic acid target is a relatively more rare or optionally a more unstable nucleic acid species when compared to even other nucleic acids that are derived from the same organism form.

One currently favored approach is thus to construct and screen libraries derived from a single organism source. However, the isolation of a single organism species from the rich complexity of an environmentally derived sample often requires culturing or other separation approaches to achieve homogeneity, and consequently this approach is frequently problematic and painstaking, if not unfeasible. Specifically, it has become increasingly appreciated that within the often rich complexity of an environmentally derived sample there may exist (1) a desirable source organism that possesses poorly understood culturing requirements and/or responses, (2) a desirable source organism that is problematic to culture, (4) a desirable source organism that is poorly characterized, and hence is not easily separable or distinguishable, and (5) at least two groupings of culturable but not easily separable organisms that possess incompatible culturing requirements and/or dissimilar culturing responses. Moreover, (5) the abundance of a desired nucleic acid may be prohibitively low even within a single organism species. Alternatively, (6) the abundance of a desired nucleic acid may become drastically diminished upon the subjection its source organism to culturing. Potentially still, (7) the screening process employed may require that there be an exaggerated proportional representation of a desired constituent in order for its presence to be positively identified above, e.g., the background signal. On the other hand, (8) it may be desirable to have a means to access a plurality of heterogeneous organism forms in parallel rather than in series.

The common result, nonetheless, is that—due to logistical considerations—a desired target in a library may be so overwhelmingly outnumbered by undesired components—and particularly by redundant undesired components—that it resembles a needle concealed in a forbiddingly large haystack. Accordingly, the size of the library that must be screened to expect a reasonable chance of success becomes essentially unmanageable. Thus, a particularly desired nucleic acid may be prone to virtual "loss" when subjected to conventional library construction processes and hence becomes unrecoverable during the ensuing screening processes.

In consequence, novel methods to overcome these logistical impediments are highly desirable. In particular, the screening of mixed populations of organisms is a desirable option. However, previously attempts at screening mixed populations were unfeasible if not impractical and were avoided because of the cumbersome procedures required.

A Specific Example of the Problem to be Solved:

A particular embodiment of the problem addressed by the instant invention is exemplified by, but by no means limited to, the following issue encountered in the area concerned with the search for novel microbial enzymes. Specifically, this area is concerned with the increasing demand in the research reagent, diagnostic reagent, and chemical process industries for protein-based catalysts possessing novel capabilities. At present, this need is largely addressed using enzymes purified from a variety of cultivated bacteria or fungi. However, because less than 1% of naturally occurring microbes can be grown in pure culture (Amann, 1995), alternative techniques must be developed to exploit the full breadth of microbial diversity for potentially valuable new products.

Virtually all of the commercial enzymes now in use have come from cultured organisms. Most of these organisms are bacteria or fungi. Amann et al. (Amann, 1995) have estimated the culturability of microorganisms in the environment as follows:

| Habitat | Culturability (%) |
| --- | --- |
| Seawater | 0.001-0.1 |
| Freshwater | 0.25 |
| Mesotrophic lake | 0.01-1.0 |
| Unpolluted esturine waters | 0.1-3.0 |
| Activated sludge | 1.0-15.0 |
| Sediments | 0.25 |
| Soil | 0.3 |

These data were determined from published information regarding the number of cultivated microorganisms derived from the various habitats indicated.

Other studies have also demonstrated that cultivated organisms comprise only a small fraction of the biomass present in the environment. For example, one group of workers recently reported the collection of water and sediment samples from the "Obsidian Pool" in Yellowstone National Park (Barns, 1994) where they found cells hybridizing to archaea-specific probes in 55% of 75 enrichment cultures. Amplification and cloning of 16S rRNA encoding sequences revealed mostly unique sequences with little or no representation of the organisms which had previously been cultured from this pool, suggesting the existence of substantial diversity of archaea with so far unknown morphological, physiological and biochemical features. Another group performed similar studies on the cyanobacterial mat of Octopus Spring in Yellowstone Park and came to the same conclusion, namely, tremendous uncultured diversity exists (Ward, 1990). Giovannoni et al. (1990) and Torsvik et al. (1990a and 1990b) have reported similar results using bacterioplankton collected in the Sargasso Sea and in soil samples, respectively. These results indicate that the exclusive use of cultured organisms in the screening for useful enzymatic or other bioactivities severely limits the sampling of the potential diversity in existence.

The screening of gene libraries from cultured samples has already proven valuable. It has recently been made clear, however, that the use of only cultured organisms for library generation limits access to the diversity of nature. The uncultivated organisms present in the environment, and/or enzymes or other bioactivities derived thereof, may be useful in industrial processes. The cultivation of each organism represented in any given environmental sample would require significant time and effort. It has been estimated that in a rich sample of soil, more than 10,000 different species can be present. It is apparent that attempting to individually cultivate each of these species would be a logistical impracticality. The alternative approach, specifically, to generate and screen a library that contains a raw and unfiltered proportional representation of all the organisms in the soil sample, likewise presents a logistical impediment. Therefore, novel methods of efficiently accessing the diversity present in the environment are highly desirable.

SUMMARY OF THE INVENTION

The present invention overcomes the logistical obstacles encountered when existing technologies employing conventional unadjusted nucleic acid libraries are applied to the screening of an environmentally derived library, by disclosing a technology for the construction and use of a nucleic acid library that contains advantageously adjusted proportions of defined components. Specifically, the instant technology provides a means for constructing a library that is catalogued, i.e. it is characterized with respect to contents, and that is preferably further normalized or enriched with respect to defined components.

By expanding previous logistical frontiers this invention allows for a novel generation of previously unattainable molecules—particularly molecules that are "unclonable" from conventional, unadjusted libraries—to now be detected, cloned, manipulated, expressed, studied, and used. The present invention achieves this goal by providing methods to isolate the nucleic acid molecules from a variety of sources, including eukaryotic cells and tissues, isolated organisms, consortia of microorganisms, primary enrichments, and environmental samples to make libraries in which defined components have been advantageously adjusted with respect to their original representation in the sample sources. Libraries thus constructed can be feasibly screened with respect to the molecular structures and/or the corresponding activities of the component molecules.

In one embodiment, the present invention represents a novel, recombinant approach to generate and screen nucleic acid libraries constructed from mixed organism populations of cultivated or, preferably, uncultivated (or "direct environmental") samples. In accordance with the present invention, libraries with normalized representations of genomes or other nucleic acids from organism that can differ vastly in abundance in natural populations can be generated and screened. This "normalization" approach reduces the redundancy of clones from abundant species and increases the proportional representation of clones from rare species. These normalized libraries are endowed with enhanced yield potentials and allow for greater screening efficiency in the search for genes encoding novel biological catalysts.

Alternatively, in another embodiment, libraries generated according to the instant invention contain an enhanced proportional representation of defined nucleic acids—or groups thereof. This is particularly applicable when a desired library constituent is known to correlate with one or more detectable parameters, particularly when these detectable parameters are serviceable for positively and/or negatively selecting library constituents so as to construct an enriched library.

In sum, the screening of a catalogued library, particularly when the library is further normalized or selectively enriched, provides a means for achieving an enhanced yield potential when compared to the screening of an uncatalogued and furthermore unadjusted library.

Accordingly, the screening of mixed populations of organisms has been made a rational approach because of the availability of techniques described herein, whereas previously attempts were unfeasible if not impractical and were avoided because of the cumbersome procedures required.

Thus, in one aspect the instant invention provides a process for forming a catalogued nucleic acid library from an organism sample comprised of a plurality of organism forms, by (a) forming a derived organism sample from an initial organism sample, such that the proportional representations of the constituents in said derived organism sample are adjusted to advantage by performing in any order, and at least one time, at least one step selected from the group consisting of: (i) subjecting a working organism sample to a process of selection, and (ii) recovering a fraction of a working organism sample having at least one desired characteristic; (b) isolating an initial nucleic acid sample from said derived organism sample; and (c) forming a derived nucleic acid library from said initial nucleic acid sample, such that the proportional representations of the constituents in said nucleic acid library are adjusted to advantage by performing in any order, and at least one time, at least one step selected from the group consisting of: (i) subjecting a working nucleic acid sample to a period of selection, (ii) recovering a fraction of a working nucleic acid sample having at least one desired characteristic, and (iii) assembling a working nucleic acid sample into a nucleic acid library.

Thus, in one preferred embodiment of this aspect, the process comprises the step of recovering a fraction of working organism sample having at least one desired characteristic.

In another preferred embodiment of this aspect, the process comprises the step of subjecting a working organism sample to a process of selection, during which there may be positive selection or alternatively negative selection or alternatively both. The process of subjecting a sample to positive or negative selection; may comprise selectively adjusting both the proportional representation and the population number of at least one component in a sample.

In another a preferred embodiment of this aspect, both the step of (i) recovering a fraction of a working organism sample, and the step of (ii) subjecting a working organism sample to a process of selection are performed. This may be accomplished by performing either in series or in parallel the steps of resolving the heterogeneity of a working organism sample according to at least one organism marker, and of forming a derived organism sample that is selectively enriched with respect to the resolved heterogeneity.

According a preferred embodiment of this aspect, either the step of (i) recovering a fraction of a working organism sample, or the step of (ii) subjecting a working organism sample to a process of selection may precede the other step. Additionally, either the step of (i) recovering a fraction of a working organism sample, or the step of (ii) subjecting a working organism sample to a process of selection—or alternatively both these steps—may be repeated at least once.

In one preferred embodiment of this aspect, the process comprises the step of recovering a fraction of a working nucleic acid sample having a desired characteristic.

In another preferred embodiment of this aspect, the process comprises the step of subjecting a working nucleic acid sample to a process of selection, during which there may be positive selection or alternatively negative selection or alternatively both.

In another a preferred embodiment of this aspect, both the step of (i) recovering a fraction of a working nucleic acid sample, and the step of (ii) subjecting a working nucleic acid sample to a process of selection are performed.

According a preferred embodiment of this invention, either the step of (i) recovering a fraction of a working nucleic acid sample, or the step of (ii) subjecting a working nucleic acid sample to a period of enrichment may precede the other step. Additionally, either the step of (i) recovering a fraction of a working nucleic acid sample, or the step of (ii) subjecting a working nucleic acid sample to a period of enrichment—or alternatively both these steps—may be repeated at least once.

Another aspect the instant invention provides a catalogued nucleic acid library formed from an organism sample comprised of a plurality of organisms by the process comprising the steps of (a) forming a derived organism sample from an initial organism sample, such that the proportional representations of the constituents in said derived organism sample are adjusted to advantage by performing in any order, and at least one time, at least one step selected from the group consisting of: (i) subjecting a working organism sample to a process of selection, and (ii) recovering a fraction of a working organism sample having at least one desired characteristic; (b) isolating an initial nucleic acid sample from said derived organism sample; and (c) forming a derived nucleic acid library from said initial nucleic acid sample, such that the proportional representations of the constituents in said nucleic acid library are adjusted to advantage by performing in any order, and at least one time, at least one step selected from the group consisting of: (i) subjecting a working nucleic acid sample to a period of selection, (ii) recovering a fraction of a working nucleic acid sample having at least one desired characteristic, and (iii) assembling a working nucleic acid sample into a nucleic acid library; so as to form an advantageously adjusted nucleic acid library from an organism sample.

The various preferred embodiments described with respect to the above method aspect of the invention are likewise applicable with regard to this aspect of the invention.

DEFINITIONS OF TERMS

Terms Concerned with "Nucleic Acid Molecules":

As used herein, a "nucleic acid molecule" is comprised of at least one base or one base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. Preferably the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. Preferably, the collection of molecules comprising a library is searchable and separable according to individual nucleic acid molecule species.

Terms Concerned with "Organisms":

As used herein, "organisms" of interest are sources of one or more nucleic acids. An "organism" may be eukaryotic or alternatively non-eukaryotic or alternatively prokaryotic or alternatively non-prokaryotic or alternatively viral or alternatively non-viral in origin, and may be classified as living or alternatively non-living or alternatively dead. Additionally, an "organism" is considered a nucleic acid source if it contains information that can be encoded, or alternatively stated, in nucleic acid form, regardless of whether said information is initially in nucleic acid from, and regardless of whether or not such an organism is already known to exist. Thus, by way of example, but not limitation, certain organisms, such as prions, are currently thought to be devoid of DNA (Prusiner, 1994); yet this finding alone would not eliminate them from classification as "organisms".

A specific "organism form" is defined by the particular species or alternatively strain or alternatively type or alternatively other specific grouping to which it belongs as may be implied by context. An "organism form" may be further defined by its stage in development or growth, as well as by any other characteristic that differentiates it further from other organisms.

Relevant "environmental" sources of organisms include any naturally occurring environments. Additionally, relevant "environmental" sources of organisms may include any pseudo-natural environments, i.e. an environment affected by the hand of man, that is a subset of a larger naturally occurring environment. In a non-limiting exemplification, such a pseudo-natural environment may be created purposely for the collection or harvesting of organisms, such as in the case of an "organism trap". In an alternative non-limiting exemplification, the original creation of such a pseudo-natural environment may be have been principally unrelated to the purpose of collecting or harvesting organisms, such as in the case of an ocean-bottom ship wreck, or a waste disposal site.

An "uncultured" or "uncultivated" organism is one that has not been purposely exposed to any substantial period of culturing for the explicit purpose of amplifying the organism. However, an organism is considered "uncultured" or "uncultivated" if it is exposed to a period of culturing for an incidental purpose, as exemplified by, but not limited to, the performance of a diagnostic test on the organism, transportation purposes, and the purification or isolation of the organism.

A "first generation" organism is one that remains essentially unreplicated after sampling from its natural environment, regardless of whether it is—or alternatively is not—uncultured.

A "direct environmental sample" is a sample that is uncultivated subsequent to the harvesting of the sample.

Terms Concerned with the Inventive Process and Product by Process:

A "working" sample simple refers to a sample with which one is working. Thus a "working" sample is exemplified by, but not limited to, an organism sample or, alternatively, a nucleic acid sample that is to be subjected to a processing step.

A "fraction" of a sample is used herein to mean a subset of said sample that is greater than 0% but does not exceed 100% of said sample. Thus, in one embodiment, a fraction of a sample is significantly smaller than said sample. Yet in an extreme embodiment a "fraction" of a sample may be identical to said sample. Accordingly, the proportional representation of the constituents in a fraction of a sample may be identical or alternatively similar or alternatively dissimilar when compared to that of said sample.

A sample that is "catalogued" refers to a sample that is characterized with respect to its contents. This characterization may be specific or broad. According to one particular embodiment, a nucleic acid library is catalogued when a description of the source sample is available. According to yet another particular embodiment, a nucleic acid library is catalogued when a description of a processing step to which it has been subjected is available. Accordingly, in a particular non-limiting exemplification, a nucleic acid library may be broadly characterized as simply being derived from a defined environmental soil sample. Alternatively, in another non-limiting exemplification, a nucleic acid library may be more narrowly characterized as having a normalized representation of defined components.

The process of subjecting a working sample to "a process of selection" is in reference to a process in which there may be positive selection or alternatively negative selection or alternatively both. Additionally, "a process of selection" may comprise amplifying a sample, as exemplified by but not limited to, the formation of second-generation components and possibly subsequent generations of components. Relevant components that may be amplified include, but are not limited to, organisms and nucleic acids.

The process of amplifying a sample may or alternatively may not result in the loss or alteration of a fraction of the components in a working sample. This is exemplified in a non-limiting fashion by a division of a first generation cell into two second generation cells, such that the original first generation cell is lost.

"Adjusting to advantage" is used as a collective term to encompass any adjustment that may be considered desirable or advantageous when applied to the unadjusted situation, including no adjustment. Thus, an advantageous adjustment may comprise selectively adjusting both the proportional representation and the population number of a constituent in a sample. By way of example, but not limitation, an advantageous adjustment may comprise recovering a fraction of a working sample. In yet another embodiment an advantageous adjustment may comprise subjecting a working sample to at least one processing step in addition to recovering a fraction of the working sample.

In one embodiment, "advantageously adjusting" an organism sample is exemplified by, but not limited to, subjecting a working organism sample to a process of selection during which any of the following may occur either alone or in combination: (1) positive selection, (2) negative selection, and (3) selective identification. This may be followed by the recovery of a fraction of the working sample.

In one embodiment, "advantageously adjusting" the proportional representation of the constituents of a nucleic acid may comprise selectively adjusting both the proportional representation as well as the copy number of the library constituents. This may involve any of the following may either alone or in combination: (1) positive selection, (2) negative selection, and (3) selective identification. This may be followed by the recovery of a fraction of the working sample.

In a particularly preferred embodiment, "advantageously adjusting" the proportional representation &/or the copy number of the components in a sample is comprised of resolving the heterogeneity of the sample according to at least one marker, and of forming a derived sample that is selectively enriched with respect to the resolved heterogeneity.

"Positive selection" refers to the inclusion of a positively selected target. In a non-limiting manner, the definition of "positive selection" of an organism target encompasses: (1) allowing the survival and/or growth of a significant portion of an organism target, (2) stimulating the survival and/or growth of a significant portion of an organism target (3) recovering a significant portion of an organism target, and (4) retaining a significant portion of an organism target in a working sample upon forming a derived sample.

"Negative selection" refers to the exclusion of a negatively selected target. In a non-limiting manner, the definition of "negative selection" of an organism target encompasses: (1) not allowing the survival and/or the growth of a significant portion of an organism target, (2) not stimulating the survival and/or the growth of a significant portion of an organism target (3) omitting a significant portion of an organism from targeted recovery, (4) omitting a significant portion of an organism from retention upon forming a derived sample, and (5) destroying a significant portion of an organism target.

In a non-limiting manner, the definition of "positive selection" of a nucleic acid target encompasses: (1) allowing the conservation of a significant portion of a nucleic acid target, (2) stimulating the amplification of a significant portion of a nucleic acid target, including by PCR (3) recovering a significant portion of a nucleic acid target, and (4) retaining a significant portion of a nucleic acid target in a working sample upon forming a derived sample.

In a non-limiting manner, the definition of "negative selection" of a nucleic acid target encompasses: (1) not allowing the conservation of a significant portion of a nucleic acid target, (2) not stimulating the amplification of a significant portion of a nucleic acid target, (3) omitting a significant portion of a nucleic acid from targeted recovery, (4) omitting a significant portion of a nucleic acid from retention upon forming a derived sample, and (5) destroying a significant portion of a nucleic acid target.

To "normalize" a sample refers to subjecting the sample to a process such that the proportional representation of each of the components is resultantly made more comparable if not virtually indistinguishable. Accordingly, in one embodiment, "normalization" is exemplified by, but not limited to, reducing the redundancy of clones from overly abundant species, or alternatively increasing the proportional representation of clones from rare or underrepresented species, or both.

To "selectively enrich" (or "enrich" for short) a sample refers to subjecting the sample to a process such that the proportional representation of at least one component or group of components is resultantly enhanced.

In a particularly preferred embodiment, a library that contains an advantageously adjusted representation of defined components is exemplified by, but not limited to, a "normalized" library, or alternatively a "selectively enriched" library. Accordingly, an advantageous adjustment is intended to produce an increase in a "yield potential".

The "yield potential" of a library refers in general to the probability or likelihood that using the library will generate a desirable yield. The specific conditions of usage and the specific type of yield desired define a "yield potential". Accordingly, when a library is screened for the presence of a desired constituent, the "yield potential" of a library may be related to the proportional representation of said desired constituents in the library. By way of example, but not limitation, if the desired constituent is a bacterially-derived nucleic acid, then the yield potential is expected to be higher when screening a nucleic acid library that is constructed from (1) a sample that is rich in bacterial organisms than (2) a sample comprised mainly of non-bacterial organisms with only a minimal bacterial presence.

Additionally, the "yield potential" of a library may be affected by factors that are unrelated to the proportional representation of a desired constituent, such as the suitability for use under a given set of conditions. By way of example, but not limitation, if a yeast two-hybrid approach is used to screen for a hypothetical molecule "x" in a nucleic acid library that is rich in said hypothetical molecule "x", the yield potential may nonetheless be low if one of the vectors used contains an insert that interferes with a necessary selection marker.

"Signature characteristics" of interest are those that are serviceable for analyzing and/or selecting defined sample components. A "signature characteristic" that is common to a grouping of sample components may be termed a "consensus signature characteristic" in reference to said grouping.

By way of example, but not limitation, "signature characteristics" may be serviceable in a non-exclusive manner under one or more of the following entity classifications: molecules, attributes related to molecules, biochemical pathways, attributes related biochemical pathways, physico-chemical entities, and attributes related to physico-chemical entities.

A "signature characteristic" that is relevant to an organism or alternatively to a grouping of organisms may be referred to as an "organism marker". Additionally, a "detectable parameter" that is relevant to the "signature characteristic" of an organism may also be referred to as an "organism marker".

A "signature characteristic" that is relevant to a nucleic acid or alternatively to a grouping of nucleic acids may be referred to as a "nucleic acid marker". Additionally, a "detectable parameter" that is relevant to the "signature characteristic" of a nucleic acid, or to grouping of nucleic acids, may also be referred to as an "nucleic acid marker".

Moreover, in a particular embodiment, a specific "organism marker" may also be a "nucleic acid marker".

In a particular embodiment, an "organism marker" may be exemplified by, but not limited to, one of the following: a cell surface marker; a secretable marker; a releasable marker; an incorporable marker; an intracellular marker; a marker recognized by any reagent, such as a marker recognized by a phage or by any one or more organisms; a nucleic acid marker; an organelle-associated marker; a morphological marker; a gross behavioral marker; a biochemical a process; or any one or more of the above in combination.

In a particular embodiment, a "nucleic acid marker" may be exemplified by, but not limited to one of the following: a nucleic acid sequence, an expressed protein product of a nucleic acid, a biochemical process related to an expressed protein product of a nucleic acid.

Detectable "parameters" of interest include those that are serviceable for detecting the presence of one or more signature characteristics. By way of examplification, but by no means limitation, a detectable "parameter" may include: (1) a detectable binding—or alternatively hybridization—event as an index of the presence of one or more molecules; (2) a detectable generation of a reaction product as an index of the presence of a biochemical process; (3) a detectable growth behavior as an index of the expression of a growth-altering molecule; (4) a density gradient centrifugation characteristic as an index of a gross property of a component in a sample; (5) a viability response as an index of an organism's compatibility with a set of defined growth conditions; and (6) a bioactivity, such as an effect on other organisms, as an index of the presence of a polyketide.

In sum, relevant detectable parameter include any experimentally detectable parameter, including those detectable by the senses of sight, sound, taste, touch or smell. Moreover, a relevant detectable parameter may comprise a plurality of any parameters, whether instantly mentioned or not, in combination.

BRIEF DESCRIPTION OF THE DRAWINGS

FIG. 2 is a schematic illustration of a preferred aspect of the present invention, which comprises the step of advantageously adjusting the proportional representation of a plurality of components in a working sample. Illustrated, by way of non-limiting example, is the approach of normalizing the proportional representation of the components in a sample when said components are resolved into of a plurality of groupings according to one or more parameters. As an alternative to normalization, a working sample may be subjected to positive selection or alternatively to negative selection or alternatively to both positive and negative selection, such that the proportional representation of one or more specific groupings is selectively adjusted.

Figure 1:
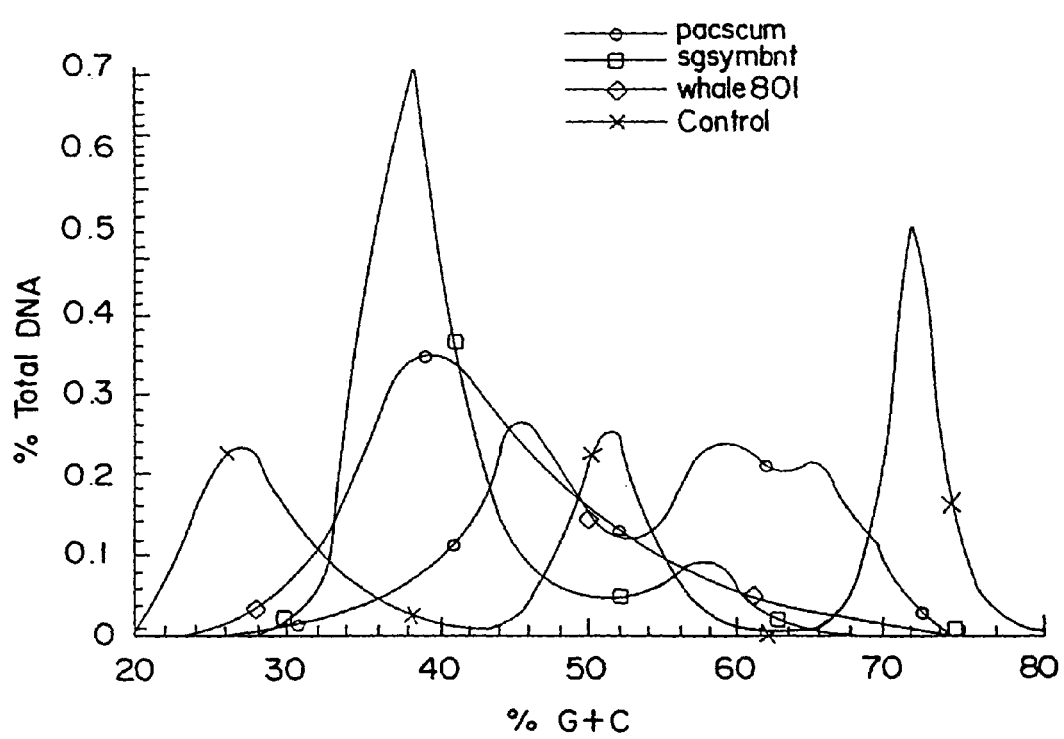
FIG. 1 is a graph showing the correlation between the proportional representation of the total DNA content and the G+C content for various genomic DNA isolates tested as described in Example 4.

Panel A illustrates a situation where the heterogeneity of a working sample is resolved according to a single continuous parameter, termed "Continuous Parameter #1". In general, the components of a working sample can be resolved into a plurality of groupings comprised of a potentially very large number of groupings. For the sake of illustration, only two groupings are shown. These two groupings are represented by two corresponding areas, each of which is delineated upwardly by a local peak and horizontally by consecutive nadirs. While the two peaks shown are essentially of the same height, the corresponding areas under the curve are dissimilar because the nadirs are unevenly spaced. Hence, to advantageously adjust the proportional representation of each grouping, recovery limits, portrayed by the finite areas enclosed within each pair of dashed lines, may be applied in order to recover a normalized working sample.

Panel B illustrates a situation where the heterogeneity of a working sample is resolved according to a single continuous parameter, termed "Continuous Parameter #1". In general, the components of a working sample can be resolved into a potentially very large number of groupings. For the sake of illustration, only two groupings are shown. These groupings are represented by two corresponding areas, each of which is delineated upwardly by a local peak and horizontally by consecutive nadirs. While the nadirs are essentially evenly spaced, the demarcated areas under the curve are dissimilar because the two peaks are of different heights. Hence, to advantageously adjust the proportional representation of each grouping, horizontal limits of the type shown in Panel A, portrayed by pairs of dashed lines enclosing finite areas, may be applied in order to recover a normalized working sample. Furthermore, because the two peaks are of different heights, an upward recovery limit, portrayed by the horizontal dashed line, may be applied, either alone or in combination with one or more additional recovery limits, in order to enhance the degree of normalization.

Panel C illustrates a situation where the heterogeneity of a working sample is resolved according to a single continuous parameter, termed "Continuous Parameter #1". For the sake of illustration, a situation is shown where a sample is resolved into a very large number of groupings. Individual areas under the curve, each delineated upwardly by a local peak and horizontally by consecutive nadirs, portray the proportional representation of each grouping. In the illustrated situation, the demarcated areas under the curve are dissimilar both because the nadirs are unevenly spaced, and because the peaks shown are of different heights. In this type of situation, particularly because there is a very large number of dissimilar peaks, a non-limiting approach to normalize the different proportional representations is comprised of applying a single vertical recovery limit, as portrayed by the horizontal dashed line, in order to obtain a normalized working sample.

Panel D illustrates a situation where discrete parameters, termed "#1" and "#2", are serviceable for resolving the heterogeneity of a working sample. In general, the components of a working sample can be resolved according to a very large number of discrete parameters. For the sake of illustration, only two groupings are shown, which are represented by bars of different heights. To advantageously adjust the proportional representation of each grouping, an upward recovery limit portrayed by the horizontal dashed line, is applied in order to recover a normalized working sample. In a non-limiting manner, a discrete parameter may be exemplified by a detectable hybridization to a discrete marker such as a particular 16S rRNA probe.

Panel E illustrates a situation where two continuous parameters, termed "Continuous Parameter #1" and "Continuous Parameter #2", respectively, are each serviceable for resolving the heterogeneity of a working sample. Specifically, different groupings result when the components are resolved according to "Continuous Parameter #1" than when resolved according to "Continuous Parameter #2". Furthermore, by considering the two parameters in combination, the components can be further regrouped into novel distinguishable groupings. For the sake of illustration, five of these novel groupings are shown, based on the dual consideration of both parameters. In the illustrated situation the volume enclosed by each three-dimensional hill represents an individual population. To advantageously adjust the proportional representation of each grouping, it may be prudent in certain instances to apply a recovery limit, portrayed by the cylindrical volumes demarcated with dashed lines, in order to recover a normalized working sample. Moreover, an upward recovery limit, that is not portrayed in the illustration but may be visualized as a horizontal plane, may be applied, either alone or in combination with one or more additional recovery limits, in order to approach perfect equalization more closely. Alternatively, recovery limits may be applied differentially to different groupings in order to selectively enrich for specific targeted components.

It is noteworthy that the experimenter can advantageously select a panel of serviceable parameters based on both the specificity of each parameter as well as the total number of parameters to be used. Moreover, it is generally the case that the specificity of each parameter is inversely proportional to its inclusiveness. In a particular exemplification, it may be desirable to select a panel of discrete parameters that are not mutually exclusive of each other when used in combination. This is particularly relevant when the panel of discrete parameters is being chosen for use in the normalization of a working sample, and particularly when the sample is thought to contain poorly characterized or unknown components. It would be an objective, in this case, to maximally retain the heterogeneity of the working sample while limiting the recovery of only the overly redundant components. Accordingly, it would be desirable, in this case, to select a panel of discrete parameters that have broad coverage and, consequently, some mutual overlap.

Panels A through E in FIG. 2 are provided merely as illustrative, but by no means limiting, examples of the available and pertinent approaches that can be used to normalize the components of a sample according to the instant disclosure. Furthermore, Panels A through E in FIG. 2 are illustrative, in a non-limiting fashion, of approaches that can be used to enrich for specific targeted components of a sample according to the instant disclosure.

By way of a particular non-limiting aspect, a sample comprised of unequally represented heterogeneous components may be resolved according to a parameter that encompasses all of the components. The profile of a normalized sample may be represented by a bell-shaped curve or alternatively a bimodal distribution rather than by a horizontal line. For example, it may be known that a specific sample comprised of 1000 heterogeneous molecules yields a bell-shaped profile when resolved according to size. With this knowledge, it may then be desirable to normalize a different sample in which the same 1000 molecular species are unequally represented. Thus, an advantageous adjustment, in which a bell-shaped recovery limit is applied, results in the formation of a sample that is selectively enriched with respect to the parameter of size, yet normalized with respect to the representation of the 1000 molecular species.

Thus, in accord with the present invention, recovery limits can be applied using a variety of approaches in order to achieve an advantageously adjusted sample. Moreover, in accord with the present invention, recovery limits can be

DETAILED DESCRIPTION OF THE INVENTION

Forming a Derived Organism Sample:

In accordance with the instant invention, an initial way to catalogue a nucleic acid library to be generated is comprised of obtaining a description of the location, e.g. environmental source, from which the organism source sample is obtained. In a particularly preferred embodiment, a nucleic acid library can be further catalogued by resolving the heterogeneity of a working organism source sample prior to isolating a nucleic acid sample from the source sample. In another particularly preferred embodiment, organisms are further subjected to a selection process according to defined organism markers. In yet another particularly preferred embodiment, an organism sample that is resolved according to at least one organism marker is further advantageously adjusted according to the resolved heterogeneity. In a particular aspect, an organism marker may also serve simultaneously as a nucleic acid marker.

The instant invention is particularly applicable to samples comprised of a plurality of unlike components, particularly when the unlike components furthermore have unlike proportional representations. As illustrated in FIG. 2, the approach of the instant invention is comprised of resolving the heterogeneity of the components in a working sample according to parameters that are serviceable for discriminating the heterogeneity of the components. As illustrated in FIG. 2, the approach of the instant invention is further comprised of applying recovery limits to the resolved heterogeneity in order to advantageously adjust the proportional representation of the working plurality of components. The approach illustrated in FIG. 2 is applicable to a variety of relevant sample components including, by way of non-limiting example, organisms in an organism sample and nucleic acids in a nucleic acid sample.

However, it is particularly relevant to the instant invention that, in the realm of novel or incompletely characterized organisms, high-specificity markers, such as specific surface markers, may sometimes be scantily available. For this reason, approaches based on the use of a large number of very high-specificity organism markers may sub-optimal, e.g. there may not be enough available markers to resolve the entire sample. Accordingly, it may be preferential in those instances to use approaches involving fewer relatively lower-specificity markers. In a particular exemplification, relatively lower specificity markers may be used that are based on consensus signature characteristics belonging to a relatively large grouping of sample constituents, such as certain 16S rRNA probes. Alternatively, parameters of relatively even lower specificity can be used, based on size and composition, such as electrophoretic migration or sedimentation or centrifugation characteristics or the relative G+C content of the nucleic acid.

Thus, as illustrated in FIG. 2, main approach of the instant invention involves the process of resolving the heterogeneity of a plurality of components in a sample according to markers that allow maximal retention of the heterogeneity of the sample, and in particular markers that are inclusive of potentially desirable but rare components. Moreover, serviceable markers include those that markers allow the resolution of overly abundant components from rare components. In general, the higher the inclusiveness of a marker, the lower the specificity of said marker. Thus, in a particularly preferred aspect of the instant invention, the heterogeneity of a working sample may be resolved according to relatively fewer low-specificity organism markers or nucleic acid markers. Alternatively, the heterogeneity of a working sample may be resolved according to relatively more high-specificity organism markers or nucleic acid markers.

In a particularly relevant embodiment of the instant invention, the components of an organism sample are advantageously adjusted according to one or more organism markers prior to the isolation of a nucleic acid sample from said organism sample.

As shown in FIG. 2, the heterogeneity of the components of a sample may be resolved into more than one grouping by using one or more detectable parameters. Moreover, as shown in FIG. 2, the proportional representation of each grouping may be different. Accordingly, an advantageous adjustment may be performed to obtain a more desirable proportional representation of each grouping. According to a particularly preferred embodiment, an advantageous adjustment is comprised of normalizing a working sample by applying recovery limits to one or more groupings of components. According to yet another preferred embodiment of this invention, an advantageous adjustment is comprised of selectively enriching for targeted components in a sample by differentially applying recovery limits to one or more groupings of components.

Thus, in a preferred embodiment of the disclosed invention, the heterogeneity of an organism sample is resolved. In yet another preferred embodiment of the disclosed invention, a derived organism sample is formed from an initial organism sample. In a particularly preferred embodiment, the step of resolving the heterogeneity of an organism sample is performed in conjunction with the formation of a derived organism sample from an initial organism sample. In an alternatively preferred embodiment, the step of resolving the heterogeneity of an organism sample may be separated from the step of forming a derived organism sample from an initial organism sample.

According to one embodiment the instant invention, the step of resolving the heterogeneity of a working sample is comprised of resolving the heterogeneity of a fraction of a parent working sample, which fraction may or may not be a representative fraction. The step of resolving the heterogeneity of any parent sample may be repeated at least once, using either the same parameters or different parameters in the analyses, and using either the same fraction or different fractions of the parent sample. Following an analysis, an analyzed fraction either may or alternatively may not be resultantly recoverable for the isolation of nucleic acids therefrom. Thus, a fraction of a sample may be terminally expended by subjecting it to analysis.

According to the instant invention, there is a wide range of relevant degrees from which to choose a suitable degree of specificity when an organism sample is subjected to analysis and/or to a selection process, and whether the selection is positive or negative or both. Thus, it may preferable on some occasions to employ a relatively low-specificity step. Alternatively, it may be preferable on other occasions to employ a relatively high-specificity step. Hence, in accordance with this invention, the specificity of a selection process to which an organism sample is subjected can also be varied to advantage.

Markers and Reagents Serviceable for Forming a Derived Organism Sample:

In general, an organism marker may be exemplified by, but not limited to, one of the following: any incorporable marker, any marker recognized by any reagent, any nucleic acid marker, any organelle-associated marker, any individual or collective morphological marker, any gross behavioral marker, any biochemical process, or any one or more of the above in combination. In sum, serviceable organism markers include any organism-associated marker, including any experimentally detectable marker, whether such a marker is known to exist or whether it remains to be discovered.

Relevant Organism Markers Include any Serviceable Phenotypic Marker:

According to the instant invention, an organism marker may be comprised of any marker associated with an organism, including phenotypic and genotypic markers. Moreover, it is appreciated that the manifestation of a phenotype is routinely diagnosed using genetic markers. Likewise, the manifestation of a genotype is routinely diagnosed using phenotypic markers. Thus, it is appreciated that an advantageous adjustment of the components in a nucleic acid sample can be performed on the source organisms prior to the isolation of the nucleic acids.

In a non-limiting exemplification, a relevant phenotypic marker may be comprised of a biochemical process. Accordingly, a relevant phenotypic marker may be exemplified by a relatively widely present biochemical process. A non-limiting example of such a process may be a relatively widely present hydrolysis reaction, which may be detectable with the use of a relatively wide-spectrum reagent. A non-limiting example of such a reagent is esculin, which is hydrolyzed by a relatively wide range of microorganisms, including gram-positive and gram-negative bacteria. Esculin fluoresces at 366 nm, whereas its hydrolysis product esculetin does not. Hence the use of esculin is serviceable in a detection method that is based on the disappearance of a fluorescent signal, and that can be read in as quickly as 15 minutes (Edberg, 1976). A particular application of this approach is described in U.S. Pat. No. 5,096,668, which is incorporated herein by reference.

Optionally, a relevant organism marker may be exemplified by a relatively narrowly present biochemical process. A non-limiting example of such a process may be a relatively narrowly present hydrolysis reaction, which may be detectable with the use of a relatively narrow-spectrum reagent. A non-limiting example of such a reagent may be certain umbelliferone derivatives. A particular example is the compound 4-methylumbelliferyl galactoside, which detects galactosidase-expressing organisms (Berg, 1988). When a non-fluorescent umbelliferone derivative is hydrolyzed by a target organism, a fluorescent umbelliferone or 4-methylumbelliferone molecule is liberated, that fluoresces with a light blue color at 450 nm. Hence the use of 4-methylumbelliferyl galactoside is serviceable in a detection method that is based on the appearance of a fluorescent signal. A particular application of this approach is described in U.S. Pat. No. 4,591,554, which is incorporated herein by reference.

Furthermore, in additional embodiments, a relevant organism marker may be comprised of any serviceable biochemical process or biochemical activity or enzyme or factor. Thus, it is relevant to this invention that, by way of non-limiting example, chromogenic substrates are available—and can be used according to this disclosure—for detecting the activity of a variety of enzyme activities including, but not limited to, glycosidase, phosphatase, esterase, galactosaminidase, and aminopeptidase activities. A particular application of this approach is provided in U.S. Pat. No. 4,874,695, which is incorporated herein by reference.

Additionally still, it is relevant to this invention that, by way of non-limiting example, serviceable enzymes or enzymatic activities include any serviceable member selected from group comprised of: 1) oxidoreductases, 2) transferases, 3) hydrolases, 4) lyases, 5) isomerases, 6) ligases, and 7) nucleic acid modifying enzymes, such as restriction enzymes (International Union of Biochemistry and Molecular Biology, 1992).

According to the instant disclosure, the level of specificity attained by the screening method can be varied. Thus, by way of non-limiting example, it is possible to screen for hydrolases in general. Alternatively, by way of non-limiting example, it is possible to screen for a particular subset of the hydrolases, i.e. by screening for a particular type of bond upon which hydrolases act. The selection of a relatively lower specificity screening approach facilitates a correspondingly higher inclusiveness, and is particularly preferred in order to avoid the loss of rare species or species for which a consensus characteristic is not known with certainty.

Relevant Organism Markers Include any Serviceable Genotypic Marker:

According to this invention a relevant organism marker may also be comprised of a genotypic organism marker. In a particular embodiment of this aspect, the detection of microbial organisms can be accomplished by the hybridization of a nucleic acid probe to an organism-specific DNA to form a detectable complex. A particular application of this approach is provided in U.S. Pat. No. 4,689,295, which is incorporated herein by reference.

In a particularly preferred embodiment, one or more genotypic markers are used to type and quantify the components in an organism sample. A non-limiting example of this embodiment is the use of 18S rRNA probes for eukaryotic organisms or 16S rRNA probes for prokaryotic organisms. A particular application of this approach is provided in U.S. Pat. No. 5,422,242, which is incorporated herein by reference.

Additionally, it is well known in the art that the specificity of a detection approach based on nucleic acid hybridization can be varied according to many factors. Accordingly, it is relevant to this invention that the degree of the specificity used can be manipulated by varying factors such as the hybridization conditions, including temperature, salt concentrations, and other reagents, as well as the compatibilities and sizes of the hybridizing partners.

Detection Methods Serviceable for Forming a Derived Organism Sample:

In accordance with this invention, many detection methods can be used for analyzing and selecting defined components in an organism sample, and these are known in the art. Among the more recent developments is the use of flow cytometry-based approaches (Porter, 1993; Porter, 1996).

A particular benefit of flow cytometry is that single-cell analyses and/or sorting can be performed without the need for culturing (Desmonts et al, 1990). This benefit is particularly desirable because, in accordance with the instant disclosure, the ability to access the full diversity of environmental organisms is endowed by the ability to harvest organisms without the need for culturing.

Yet an additional benefit of flow cytometry is that it provides a means to recover cells while retaining their viability and culturability. This additional benefit is particularly desirable because, in accordance with the instant disclosure, the step of subjecting a working organism sample to a selection process may comprise a period of culturing. By way of example, but not limitation, this process is particularly desirable as an approach to enrich for a particularly rare but culturable organism or grouping of organisms. However, it must be stressed that the principal benefit of this invention is the ability to obviate the need for culturing organisms. Thus the instant invention provides a means to access the full diversity of first-generation organisms procured from their natural environments, of which approximately 99% are estimated to have not been cultured.

In accordance with the instant invention, flow cytometry can be used in a variety of ways. By using light scattering and cocktails of fluorophores, a serviceable extent of discrimination and identification is achievable upon subjecting a mixture of organisms to flow cytometric analysis (Davey and Kell, 1996). The resolution of flow cytometry is continually increasing as a result of newly available reagents from an ever-expanding list, in particular monoclonal antibodies. Technological advances, including the aid of computer software, have also enhanced the discriminating power of flow cytometry by enabling the simultaneous detection of increasing number of parameters, as exemplified by a particular description of an 8-parameter technology (Kachel, 1990).

Summarily, antibodies labeled with fluorescent tags as well as non-antibody-based molecules allow the enumeration of defined surface antigens, intracellular molecules, and other organism markers (Galbraith, 1994; Troussellier et al, 1993; Laplace-Builhe et al, 1993). Consequently, in accordance with the instant invention, the use of flow cytometry reagents is serviceable for detecting, analyzing, and sorting a variety of organisms in a mixed population.

In addition to flow cytometry, other standard techniques may be employed in accordance with the instant invention. These include standard microbiological techniques, as exemplified by, but not limited to, established techniques in microscopy and culturing, some of which have been compiled in texts (Gerhardt, 1994; Lederberg, 1992; Balows et al, 1992).

Detectable Moieties and Labels Serviceable for Forming a Derived Organism Sample:

A variety of detectable moieties and labels signals are relevant to the instant invention as understood in the art. Included also are any moieties and labels that generate a signal that is detectable by the senses of sight, sound, touch, smell, and taste. By way of non-limiting example, these include moieties and labels that generate radioactive and chromogenic signals. Furthermore, by way of non-limiting example, these moieties and labels can be comprised of at least one enzymatic, isotopic, and otherwise detectable molecule.

In one particular embodiment, fluorescent interactions and fluorescence resonance energy transfer (FRET) can be used. The use of fluorescent proteins and/or fluorescent groups and quenching groups in close proximity to one another to assay the presence of enzymes or nucleic acid sequences has been reported (IPN WO 97/28261 and IPN WO 95/13399). In the first of these reactions, fluorescent proteins having the proper emission and excitation spectra are put in physically close proximity to exhibit fluorescence energy transfer. Substrates for enzyme activities are placed between the two proteins, such that cleavage of the substrate by the presence of the enzymatic activity separates the proteins enough to change the emission spectra. Another group utilizes a fluorescent protein and a quencher molecule in close proximity to exhibit "collisional quenching" properties whereby the fluorescence of the fluorescent protein is diminished simply via the proximity of the quenching group. Probe nucleic acid sequences are engineered between the two groups, and a hybridization event between the probe sequence and a target in a sample separates the protein from the quencher enough to yield a fluorescent signal. Still another group has reported a combination of the above strategies, engineering a molecule which utilizes an enzyme substrate flanked by a fluorescent protein on one end and a quencher on the other (EPN 0 428 000). It is recognized that these types assays can be employed in the method of the present invention to detect modifications in nucleic acid production (transcriptional activation or repression) and/or enzyme or other protein production (translational modifications) which results from inhibition of or improved association of interacting molecules, such as ligands and receptors, or which results from actions of bioactive compounds directly on transcription of or particular molecules.

Probe nucleic acid sequences designed according to the method described above can also be utilized in the present invention to enrich a population for desirable clones, as previously described. For example, probes can be designed to identify specific polyketide sequences, and utilized to enrich for clones encoding polyketide pathways. Thus, this aspect of the present invention facilitates the reduction of the complexity of the original population to enrich for desirable pathway clones. These clones can then be utilized for further downstream screening. For example, these clones can be expressed to yield backbone structures, which can the be transferred into for decoration by metabolically rich hosts, and finally screened for an activity of interest. Alternatively, clones can be expressed to yield small molecules directly, which can be screened for an activity of interest. Further more, it is recognized that multiple probes can be designed and utilized to allow "multiplex" screening and/or enrichment. "Multiplex" screening and/or enrichment as used herein means that one is screening for more than desirable outcome, simultaneously.

Combinations of Approaches Serviceable for Forming a Derived Organism Sample:

In accordance with the instant invention, the formation of a derived organism sample may be achieved by the use of a combination of more than one technique as well as more than one reagent. In a particular embodiment of this aspect, an initial technique can be performed in combination with one or more additional techniques to simultaneously access the benefits of the appended techniques in order to resolve the heterogeneity of an organism sample. This manner of combining techniques is also serviceable for forming a derived organism sample from a mixed population sample. In a particular non-limiting example, the direct detection of specific nucleotide sequences localized within relatively intact cells is achievable by employing flow cytometry in combination with in situ polymerase chain reaction (Porter, 1995). This particular combination of techniques—as well as many others—can be applied with great leeway to the instant invention, because, as presently disclosed, processed organisms need not be resultantly culturable or otherwise viable, provided their nucleic acids are recoverable.

In yet another particular embodiment of this aspect, an initial reagent can be used in combination with one or more additional reagents to simultaneously access the benefits of the appended reagents in order to resolve the heterogeneity of an organism sample. This manner of combining reagents is also serviceable for forming a derived organism sample from a mixed population sample.

In a particular exemplification, a method can be used whereby detection and selection are achieved by the use a dual function medium that is specific for a target microbe. In a non-limiting example, a medium can be used that: (1) contains a key reagent that serves as a nutrient that is used essentially exclusively by a target organism, and that provides a detectable signal upon being metabolized; and (2) contains no other nutrients that could be used by non-targeted organisms. A particular application of this approach is described in U.S. Pat. No. 5,429,933, which is incorporated herein by reference. Accordingly, this type of selective medium may be termed a selective "nutrient indicator", and is known in the art.

By way of another non-limiting example, a probe comprised of a specific binding partner—such as a monoclonal antibody or alternatively a nucleic acid molecule—may be linked to magnetic beads (Haukanes, 1993). Accordingly, the specificity of the probe facilitates the recognition of a defined target, while the use of an external magnet facilitates the recovery of the targeted organism.

Bioactive Agents Serviceable for Forming a Derived Organism Sample:

In a particular embodiment of this invention, an organism sample may be subjected to a selection process by exposure to a selective reagent that is additionally a bioactive agent. In accord with this embodiment, a working sample may be subjected to a period of culturing during which first-generation organism yield younger generations. However, the main benefit of this invention is the ability to access the full diversity of organisms harvested from a natural or pseudo-natural environment, and to form a high-yielding nucleic acid library from first-generation and near first-generation organisms. Accordingly, the instant invention is applicable to and of benefit to culturable cells. Nonetheless, it is a substantial benefit of the present invention that serviceable reagents may exert their action without the need for producing subsequent generations of organisms.

In a particular embodiment, the selection process is comprised of creating a pseudo-natural microenvironment within a larger natural environment. In general, this approach may be termed "selective organism trapping", "selective organism harvesting", or "selective organism fishing". A particular embodiment of this process is performed at the step of collecting an initial organism sample using a collection device placed in an otherwise natural environment. By way of non-limiting example, this device may be comprised of a solid support containing a specific nutrient or other bioactive reagent. In this instance, the specific nutrient may serve as an agent to positively select for a targeted grouping of organisms. Alternatively, a bioactive reagent may be comprised of an agent, such as an antibiotic, that negatively selects for a targeted grouping of organisms. The selectivity of the collection device may thus be based on the presence of a biochemical process in a targeted organism that either facilitates or prevents the organism from living in the environment of the collection device.

According to this aspect, a variety of agents are known in the art and are serviceable—individually or in combination—for the positive and/or negative selection of organisms including, by way of example but not limitation: lectins, toxins, chemokines, cytokines, nutrients, antibodies, complements, and even other organisms. The use of these agents is understood in the art and is exemplified—but not limited—by those instances referenced in the selected publications (Osawa, 1988; Norris et al, 1985).

Additionally, by way of example, but not limitation, a sample may be subjected to a period of culturing involving negative selection. This may be achieved, by way of example, but not limitation, by the use of any of a variety of chemotherapeutic agents. By way of example, but not limitation, preferred chemotherapeutic agents include those in the following non-exclusive categories: anti-eukaryotic agents, antibacterial agents, antifungal agents, antiviral agents, and other antimicrobial agents.

Alternatively still, in accordance with the instant invention, the detection and/or sorting of an organism can be achieved by the use of a phage-based test (Blackburn, 1993; Sarkis, 1995). The outcome of this type of test may be designed to depend on either (1) the ability of the phage to bind specifically to a target organism, or alternatively (2) the ability of a phage to specifically infect a target organism. The difference between the two options is that the number of organisms that a phage can infect may represent a significantly smaller fraction of the total number of organisms to which said phage can bind. Accordingly, greater sensitivity is often expected when this type of test is designed to depend on phage binding. Alternatively, greater specificity is often expected when this type of test is designed to depend on phage infection.

Additional examples of reagents relevant to the instant invention, include—but are not limited to—reagents serviceable for phage-based techniques in combination with known solid support systems, other separation reagents, and reporter systems. According to a specific embodiment of this aspect, an organism-specific phage can be used to transduce, for example, a bacterial bioluminescence into a targeted organism or grouping of organisms. When infected, targeted organisms become distinguishable in a rapid detection method in which infected host organisms can be identified against a background of non-infectable organisms. According to an alternative embodiment of this aspect, an organism-specific phage that is immobilized onto a solid phase can be used to achieve the separation and concentration of a target organism. According to yet another specific embodiment of this aspect, an organism can be detected and lysed using a bacteriophage endolysin in order to recover DNA, RNA, and proteins (Loessner, 1995).

According to yet another specific embodiment of this aspect, the use of an organism-specific phage to transduce, for example, an ice-nucleation gene into infected hosts serves as a particularly useful detection method whereby results may be visualized with the naked eye. According to this approach, infected organisms express an ice nucleation product and, as a result, acquire the ability to freeze upon subjection to a critical temperature range at which uninfected organisms do not freeze. Consequently, a phage-treated organism sample may be exposed to a reagent that reveals a color change upon freezing and subjected to a critical temperature range, in order to visually identify infected target organisms against a background of non-infectable organisms. A particular application of this approach is described in U.S. Pat. No. 4,784,943, which is incorporated herein by reference. A commercial assay kit for detecting *Salmonella* based on this patent is sold under the name BIND® by Idexx Laboratories, Inc. (Westbrook Me.).

It is understood that number of organism-specific bacteriophages that are available for typing organisms, including those in the international phage set, is continually expanding (Marquet-Van der Mee, 1995), and that these phages are serviceable in this invention.

Nucleic Acid Isolation:

An important step in the generation of a normalized nucleic acid library from an environmental sample is the preparation of nucleic acid from the sample. Nucleic acids can be isolated from samples using various techniques well known in the art (Trevors, 1995). Preferably, nucleic acids obtained will be of large size and free of enzyme inhibitors and other contaminants. Nucleic acid can be isolated directly from the environmental sample (direct lysis) or cells may be harvested from the sample prior to nucleic acid recovery (cell separation). Direct lysis procedures have several advantages over protocols based on cell separation. The direct lysis approach generally provides more nucleic acid with a generally higher representation of the microbial community, however, it is sometimes smaller in size and more likely to contain enzyme inhibitors than does the cell separation technique. Very useful direct lysis techniques have recently been described which provide nucleic acid of high molecular weight and high purity (Barns, 1994; Holben, 1994). If inhibitors are present, there are several protocols which utilize cell isolation which can be employed (Holben, 1994). Additionally, a fractionation technique, such as the bis-benzimide separation (cesium chloride isolation) described below, can be used to enhance the purity of the nucleic acid.

Forming a Derived Nucleic Acid Sample by Fractionation:

It is particularly relevant to the instant invention that, in the realm of novel or incompletely characterized nucleic acids, high-specificity markers may sometimes be scantily available for the formation of an advantageously adjusting nucleic acid sample. For this reason, alternative approaches that obviate the need for a large number of very high-specificity nucleic acid markers are also provided. Accordingly, it may be preferential in some instances to use approaches involving fewer relatively lower-specificity markers as well as approaches that do not require markers at all. In a particular exemplification, relatively lower specificity markers may be used that are based on consensus signature characteristics belonging to a relatively large grouping of sample constituents, such as certain 16S rRNA probes. Alternatively, parameters of relatively even lower specificity can be used, such as size, sedimentation or centrifugation characteristics or the relative G+C content of the nucleic acid.

Thus, in a preferred embodiment of the instant invention, the heterogeneity of a nucleic acid sample is resolved according to the relative G+C content of the nucleic acid components. This resolution allows the formation of a derived nucleic acid sample in order to achieve an advantageous adjustment such as normalization or selective enrichment. The normalization of a the nucleic acid sample by fractionation as well as by other normalization approaches increases the chances of cloning nucleic acid from minor species in the pool of organisms sampled. In the present invention, nucleic acid is preferably fractionated using a density centrifugation technique. One example of such a technique comprises the use of a cesium-chloride gradient. Preferably, the technique is performed in the presence of a nucleic acid intercalating agent that will bind regions of the nucleic acid and cause a change in the buoyant density of the nucleic acid. More preferably, the nucleic acid intercalating agent is a dye, such as bis-benzimide which will preferentially bind regions of nucleic acid, such as AT regions in the specific case of bis-benzimide (Muller, 1975; Manuelidis, 1977). When nucleic acid complexed with an intercalating agent, such as bis-benzimide, is separated in an appropriate cesium-chloride gradient, the nucleic acid is fractionated. If the intercalating agent preferentially binds regions of the nucleic acid, such as GC or AT regions, the nucleic acid is separated based on the relative base content in the nucleic acid. Nucleic acid from multiple organisms can be separated in this manner.

Density gradients are currently employed to fractionate nucleic acids. For example, the use of bis-benzimide density gradients for the separation of microbial nucleic acids for use in soil typing and bioremediation has been described. In these experiments, one evaluates the relative abundance of $A_{260}$ peaks within fixed benzimide gradients before and after remediation treatment to see how the bacterial populations have been affected. The technique relies on the premise that on the average, the GC content of a species is relatively consistent. This technique is applied in the present invention to fractionate complex mixtures of genomes. The nucleic acids derived from a sample are subjected to ultracentrifugation and fractionated while measuring the $A_{260}$ as in the published procedures.

In one aspect of the present invention, equal $A_{260}$ units are removed from each peak, the nucleic acid is amplified using a variety of amplification protocols known in the art, including those described hereinafter, and gene libraries are prepared. Alternatively, equal $A_{260}$ units are removed from each peak, and gene libraries are prepared directly from this nucleic acid. Thus, gene libraries are prepared from a combination of equal amounts of nucleic acid from each peak for the purpose of normalization. This strategy enables access to genes from minority organisms, present in such minor quantities within environmental samples and enrichments, that their genomes may be underrepresented or may even lost, if a library were constructed from the total unfractionated nucleic acid sample. Alternatively, a nucleic acid sample can be subjected to one or more normalization procedures in addition to the fractionation procedure using techniques described instantly. Nucleic acid libraries can then be generated from this fractionated/normalized nucleic acid.

In another aspect of the present invention, $A_{260}$ units are removed from one or more selected peaks for the purpose of forming a derived sample that is selectively enriched with respect to the parent sample. It is particularly relevant to the instant invention that, in some cases, an increased yield potential is expected when screening a library that is selectively enriched than when screening a library that isn't. This is particularly the case when a correlation is observed between a desired yield and a particular fraction of the components for which a library can be selectively enriched. It is additionally relevant, that these types of correlations continue to be established as novel nucleic acids are discovered and knowledge about them is accumulated. In a non-limiting aspect, it is instantly relevant that the composition of multiple fractions of the fractionated nucleic acid can be determined using PCR related amplification methods of classification well known in the art.

Forming a Derived Nucleic Acid Sample by Hybridization-Based Approaches:

An additional approach that obviates the need for high-specificity nucleic acid markers comprises the use of hybridization-based approaches, where the hybridization behaviors serve as markers. In one approach, cDNA species are separated according to their duplex formation kinetics. This approach is based on the likelihood that abundant species will from duplexes more rapidly when compared to rare species. Previous normalization protocols based on hybridization kinetics have been designed for constructing normalized cDNA libraries (WO 95/08647, WO 95/11986). These protocols were originally developed for the cloning and isolation of rare cDNA's derived from mRNA. The present invention relates to the generation of normalized genomic DNA gene libraries from uncultured or environmental samples.

A related approach is based on the hybridization of cDNA species to genomic DNA. The frequency of each hybridized cDNA molecule is thus made proportional to the frequency of its genomic counterpart (Weissman, 1987). This method is likewise ineffectual for nucleic acid libraries comprised of genomic DNA species.

In contrast to the prior art cited, the present invention is manifestly serviceable for normalizing genomic DNA libraries. Additionally in contrast to the prior art cited, the present invention is serviceable for normalizing nucleic acid libraries derived from a plurality of different organisms. Accordingly, the use of certain hybridization-based approaches are relevant to the present invention. However, additional techniques are disclosed which are serviceable for replacing or supplementing the use of hybridization-based approaches. Moreover, the instant invention is not limited to the construction of a cDNA library from a single organism species. Rather, the present invention is further serviceable for the generation of normalized and selectively enriched genomic DNA gene libraries from uncultured or direct environmental samples.

Nucleic acid samples isolated directly from environmental samples or from primary enrichment cultures will typically contain genomes from a large number of microorganisms. These complex communities of organisms can be described by the absolute number of species present within a population and by the relative abundance of each organism forms within the sample. The total normalization of each organism form within a sample is very difficult to achieve. Separation techniques such as optical tweezers can be used to pick morphologically distinct members with a sample if these members are large enough. Representative members can then be combined in normalized numbers. Alternatively, pure cultures of each member within a sample can be prepared and a normalized representation of each pure culture can be combined to from a normalized working sample. In practice, this is very difficult to perform, especially in a high throughput manner.

The present invention involves the use of normalization techniques to approach perfect equalization of the genomes and other nucleic acids present within an environmental sample, generating a nucleic acid library from the normalized nucleic acid, and screening the library for an activity of interest.

In one aspect of the present invention, nucleic acid is isolated from the sample and fractionated. The strands of nucleic acid are then melted and allowed to selectively reanneal under fixed conditions ($C_o t$ driven hybridization). Alternatively, the nucleic acid is not fractionated prior to this melting process. When a mixture of nucleic acid fragments is melted and allowed to reanneal under controlled conditions, the common sequences find their complementary strands faster than the rare sequences. After an optional single-stranded nucleic acid isolation step, single-stranded nucleic acid, representing an enrichment of rare sequences, is amplified and used to generate gene libraries. This procedure leads to the amplification of rare or low abundance nucleic acid molecules. These molecules are then used to generate a library. While all nucleic acid will be recovered, the identification of the organism originally containing the nucleic acid may be lost. This method offers the ability to recover nucleic acids from "unclonable sources."

Nucleic acid samples derived using the previously described technique are amplified to complete the normalization process. For example, samples can be amplified using PCR amplification protocols such as those described by Ko and Takahashi (Ko, 1990a; Ko, 1990b, Takahashi, 1994), or more preferably, long PCR protocols such as those described by Barnes (Barnes, 1994) or Cheng (Cheng, 1994).

Normalization can be performed directly, or steps can also be taken to reduce the complexity of the nucleic acid pools prior to the normalization process. Such reduction in complexity can be beneficial in recovering nucleic acid from the poorly represented organisms. Likewise, a selective enrichment can be performed in lieu or alternatively in addition to a normalization step.

Applications of the Disclosed Advantageous Adjustments to Diverse Nucleic Acid Libraries:

In a particularly preferred, but non-limiting exemplification, nucleic acid libraries are constructed from microorganisms. Serviceable microorganisms include prokaryotic microorganisms, such as Eubacteria and Archaebacteria, and lower eukaryotic microorganisms such as fungi, some algae and protozoa. The microorganisms may be cultured microorganisms or uncultured microorganisms obtained from environmental samples and such microorganisms may be extremophiles, such as thermophiles, hyperthermophiles, psychrophiles, psychrotrophs, etc.

As indicated above, the library may be produced from environmental samples in which case the nucleic acids may be recovered without culturing of an organism or, alternatively, the nucleic acids may be recovered from a cultured organism.

Sources of microorganism-derived nucleic acid as a starting material library from which target nucleic acid is obtained are particularly contemplated to include environmental samples, such as microbial samples obtained from Arctic and Antarctic ice, water or permafrost sources, materials of volcanic origin, materials from soil or plant sources in tropical areas, etc. Thus, for example, genomic DNA may be recovered from either a culturable or non-culturable organism and employed to produce an appropriate recombinant expression library for subsequent determination of enzyme activity.

Bacteria and many eukaryotes have a coordinated mechanism for regulating genes whose products are involved in related processes. The genes are clustered, in structures referred to as "gene clusters," on a single chromosome and are transcribed together under the control of a single regulatory sequence, including a single promoter, which initiates transcription of the entire cluster. The gene cluster, the promoter, and additional sequences that function in regulation altogether are referred to as an "operon" and can include up to 20 or more genes, usually from 2 to 6 genes. Thus, a gene cluster is a group of adjacent genes that are either identical or related, usually as to their function.

Some gene families consist of identical members. Clustering is a prerequisite for maintaining identity between genes, although clustered genes are not necessarily identical. Gene clusters range from extremes where duplication is generated to adjacent related genes to cases where hundreds of identical genes lie in a tandem array. Sometimes no significance is discernable in a repetition of a particular gene. A principal example of this is the expressed duplicate insulin genes in some species, whereas a single insulin gene is adequate in other mammalian species.

It is important to further research gene clusters and the extent to which the full length of the cluster is necessary for the expression of the proteins resulting therefrom. Further, gene clusters undergo continual reorganization and, thus, the ability to create heterogeneous libraries of gene clusters from, for example, bacterial or other prokaryote sources is valuable in determining sources of novel proteins, particularly including enzymes such as, for example, the polyketide synthases that are responsible for the synthesis of polyketides having a vast array of useful activities. Other types of proteins that are the product(s) of gene clusters are also contemplated, including, for example, antibiotics, antivirals, antitumor agents and regulatory proteins, such as insulin.

Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of a huge variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

The ability to select and combine desired components from a library of polyketides and post-polyketide biosynthesis genes for generation of novel polyketides for study is appealing. The method(s) of the present invention make it possible to and facilitate the cloning of novel polyketide synthases, since one can generate gene banks with clones containing large inserts (especially when using the f-factor based vectors), which facilitates cloning of gene clusters.

Preferably, the gene cluster nucleic acid is ligated into a vector, particularly wherein a vector further comprises expression regulatory sequences that can control and regulate the production of a detectable protein or protein-related array activity from the ligated gene clusters. Use of vectors which have an exceptionally large capacity for exogenous nucleic acid introduction are particularly appropriate for use with such gene clusters and are described by way of example herein to include the f-factor (or fertility factor) of *E. coli*. This f-factor of *E. coli* is a plasmid which affect high-frequency transfer of itself during conjugation and is ideal to achieve and stably propagate large nucleic acid fragments, such as gene clusters from mixed microbial samples.

Library Screening:

After catalogued and preferably advantageously adjusted libraries have been generated, unique enzymatic activities can be discovered using a variety of solid- or liquid-phase screening assays in a variety of formats, including a high-throughput robotic format described herein. The normalization of the nucleic acid used to construct the libraries is a key component in the process. Normalization will increase the representation of nucleic acid from important organisms, including those represented in minor amounts in the sample. Selective enrichment is a particular counterpart of normalization that is additionally serviceable for enhancing the yield potential of a library for screening purposes.

A variety of standard library screening methods are available in the art. Particularly preferred approaches include expression screening. In a particular embodiment, enzymes and the nucleic acids which encode them can be identified by forming an expression library and screening the library according to groupings of enzyme activities. Further details relevant to this process are provided in co-pending application U.S. Ser. No. 08/657,409 (filed Jun. 3, 1996), and in co-pending application U.S. Ser. No. 08/692,002 (filed Aug. 2, 1996), which are both incorporated herein by reference.

EXAMPLES

Example 1

Extraction and Cleaning of Organisms from Soil (for Subsequent DNA Extraction)

The extraction method of Example 1 is based upon published methods (Holben, 1994; Rickwood, 1982) and comprises novel modifications.

A) Reagents:
1. Extraction buffer:

|  |  |
|---|---|
| MgSO4 × 7 H2O | 2.5 gm |
| NaCl | 1.25 gm |
| K2HPO4 | 2.5 gm |
| Ascorbic acid | 0.2 M |
| H$_2$O | 1.0 L |

2. Acid-washed polyvinylpolypyrrolidone (PVPP):
   Add 300 gm of PVPP to 4 L of 3 M HCl, stir overnight. Filter suspension through several layers of cheesecloth (use large Buchner funnel). Wash with 4 L distilled H$_2$O, 4 L of a 20 mM potassium phosphate buffer (pH 7.4). Repeat washes with phosphate buffer until pH is 7.0. Spread the PVPP on lab paper and let air dry overnight.
3. Nycodenz-solution:
   8 gm Nycodenz in 10 ml distilled H$_2$O.

B) Procedure:
1. Combine in a blender jar:
   50 g soil
   15 g acid-washed PVPP (polyvinylpolypyrollidon)
   200 ml extraction buffer
2. Homogenize for three 1-min intervals with 1 min cooling in an ice bath between homogenization intervals.
3. Spin down particles and eukaryotes in 500 ml tubes at 640 g, 15 min at 4° C.
4. Pour supernatant into a 500 ml centrifuge bottle and keep it on ice.
5. Resuspend soil pellet in fresh 200 ml extraction buffer.
5. Repeat blending 2 to 4 times.
6. Spin down all collected supernatants at 14,500 g in 500 ml tubes 20 min at 4° C.
7. Resuspend pellet in extraction buffer and wash several times.
8. Place sample in a centrifuge tube.
9. Place cushion of Nycodenz underneath the sample.
10. Centrifuge at 9,000 g in a swing-out rotor at 4° C. Soil particles sediment through the cushion and a relatively pure suspension of microorganisms floats at the top of the cushion.
11. Transfer layer of microorganisms into Eppi-tubes, spin down 10 min.
12. Resuspend organisms in 2×STE buffer, mix with 1% low melting agarose, and make agarose noodles.

Example 2

Genomic DNA Isolation

1. Samples are resuspended directly in the following buffer:
   500 mM Tris-HCl, pH 8.0
   100 mM NaCl
   1 mM sodium citrate
   100 g/ml polyadenosine
   5 mg/ml lysozyme
2. Incubate at 37 C for 1 hour with occasional agitation.
3. Digest with 2 mg/ml Proteinase K enzyme (Boehringer Mannheim) at 37 C for 30 min.
4. Add 8 ml of lysis buffer [200 mM Tris-HCl, pH 8.0/100 mM NaCl/4% (wt/vol) SDS/10% (wt/vol) 4-aminosalicylate] and mix gently by inversion.
5. Perform three cycles of freezing in a dry ice-ethanol bath and thawing in a 65 C water bath to release nucleic acids.
6. Extract the mixture with phenol and then phenol/chloroform/isoamyl alcohol.
7. Add 4 grams of acid-washed polyvinylpolypyrrolidone (PVPP) to the aqueous phase and incubate 30 minutes at 37 C to remove organic contamination.
8. Pellet PVPP and filter the supernatant through a 0.45 m membrane to remove residual PVPP.
9. Precipitate nucleic acids with isopropyl alcohol.
10. Resuspend pellet in 500 1 TE (10 mM Tris-HCl, pH 8.0/1.0 mM EDTA)

11. Add 0.1 g of ammonium acetate and centrifuge mixture at 4 C for 30 minutes.
12. Precipitate nucleic acids with isopropanol.

Example 3

CsCl-Bisbenzimide Gradients

Gradient Visualization by UV:
Visualize gradient by using the UV handlamp in the dark room and mark bandings of the standard which will show the upper and lower limit of GC-contents.
Harvesting of the Gradients:
1. Connect Pharmacia-pump LKB P1 with fraction collector (BIO-RAD model 2128).
2. Set program: rack 3, 5 drops (about 100 µl), all samples.
3. Use 3 microtiter-dishes (Costar, 96 well cell culture cluster).
4. Push yellow needle into bottom of the centrifuge tube.
5. Start program and collect gradient. Don't collect first and last 1-2 ml depending on where your markers are.
Dialysis
1. Follow microdialyzer instruction manual and use Spectra/Por CE Membrane MWCO 25,000 (wash membrane with ddH2O before usage).
2. Transfer samples from the microtiterdish into microdialyzer (Spectra/Por, MicroDialyzer) with multipipette. (Fill dialyzer completely with TE, get rid of any air bubble, transfer samples very fast to avoid new air-bubbles).
3. Dialyze against TE for 1 hr on a plate stirrer.
DNA Estimation with PICOGREEN
1. Transfer samples (volume after dialysis should be increased 1.5-2 times) with multipipette back into microtiterdish.
2. Transfer 100 µl of the sample into Polytektronix plates.
3. Add 100 µl Picogreen-solution (5 µl Picogreen-stock-solution +995 µl TE buffer) to each sample.
4. Use WPR-plate-reader.
5. Estimate DNA concentration.

Example 4

Bis-Benzimide Separation of Genomic DNA

A sample composed of genomic DNA from *Clostridium perfringens* (27% G+C), *Escherichia coli* (49% G+C) and *Micrococcus lysodictium* (72% G+C) was purified on a cesium-chloride gradient. The cesium chloride (Rf=1.3980) solution was filtered through a 0.2 m filter and 15 ml were loaded into a 35 ml OptiSeal tube (Beckman). The DNA was added and thoroughly mixed. Ten micrograms of bis-benzimide (Sigma; Hoechst 33258) were added and mixed thoroughly. The tube was then filled with the filtered cesium chloride solution and spun in a VTi50 rotor in a Beckman L8-70 Ultracentrifuge at 33,000 rpm for 72 hours. Following centrifugation, a syringe pump and fractionator (Brandel Model 186) were used to drive the gradient through an ISCO UA-5 UV absorbance detector set to 280 nm. Three peaks representing the DNA from the three organisms were obtained. PCR amplification of DNA encoding rRNA from a 10-fold dilution of the *E. coli* peak was performed with the following primers to amplify eubacterial sequences:
Forward primer: (27F)
5-agagtttgatcctggctcag-3 (SEQ ID NO: 1)
Reverse primer: (1492R)
5-ggttaccttgttacgactt-3 (SEQ ID NO: 2)

Example 5

Sample of DNA Obtained from the Gill Tissue of a Clam Harboring an Endosymbiont which Cannot be Physically Separated from its Host 1. Purified DNA on cesium chloride gradient according to published protocols (Sambrook, 1989).
2. Prepared second cesium chloride solution; (Rf=1.3980) filtered through 0.2 m filter and loaded 15 ml into a 35 ml OptiSeal tube (Beckman).
3. Added 10 g bis-benzimide (Sigma; Hoechst 33258) and mixed.
4. Added 50 g purified DNA and mixed thoroughly.
5. Spun in a VTi50 rotor in a Beckman L8-70 Ultracentrifuged at 33,000 rpm for 72 hours.
6. Used syringe pump and fractionator (Brandel Model 186) to drive gradient through an ISCO UA-5 UV absorbance detector set to 280 nm.

Example 6

16S rRNA Analysis 1. 16S rRNA analysis is used to resolve the heterogeneity of the DNA recovered from environmental samples (Reysenbach, 1992; DeLong, 1992; Barns, 1994) according to the protocol outlined in Example 1.
2. Eubacterial sequences are amplified using the following primers:
Forward:
5-agagtttgatcctggctcag-3 (SEQ ID NO: 1)
Reverse:
5-ggttaccttgttacgactt-3 (SEQ ID NO: 2)
Archaeal sequences are amplified using the following primers:
Forward:
5-gcggatccgcggccgctgcacayctggtygatyctgcc-3 (SEQ ID NO: 3)
Reverse:
5-gacgggcggtgtgtrca-3 (SEQ ID NO: 4) (R=purine,; Y=pyrimidine)
3. Amplification reactions proceed as published. The reaction buffer used in the amplification of the archaeal sequences includes 5% acetamide (Barns, 1994).
4. The products of the amplification reactions are rendered blunt ended by incubation with Pfu DNA polymerase.
5. Blunt end ligation into the pCR-Script plasmid in the presence of SrfI restriction endonuclease according to the manufacturer's protocol (Stratagene).
6. Samples are sequenced using standard sequencing protocols and the number of different sequences present in the sample is determined.

Example 7

Normalization

Purified DNA is fractionated according to the bis-benzimide protocols of Examples 3 and 4, and recovered DNA is sheared or enzymatically digested to 3-6 kb fragments. Lone-linker primers are ligated and the DNA is sized selected. Size-selected DNA is amplified by PCR, if necessary. Normalization is then accomplished as follows:
1. Double-stranded DNA sample is resuspended in hybridization buffer (0.12 M $NaH_2PO_4$, pH 6.8/0.82 M NaCl/1 mM EDTA/0.1% SDS).

2. Sample is overlaid with mineral oil and denatured by boiling for 10 minutes.
3. Sample is incubated at 68 C for 12-36 hours.
4. Double-stranded DNA is separated from single-stranded DNA according to standard protocols (Sambrook, 1989) on hydroxyapatite at 60 C.
5. The single-stranded DNA fraction is desalted and amplified by PCR.
6. The process is repeated for several more rounds (up to 5 or more).

Example 8 cDNA Library Construction

The construction of cDNA libraries from environmentally collected organisms is achievable according to the instant invention. In the following particular example, environmental organisms were collected at the M vent location (9° 50.29N 104° 17.48W) at a depth of 2503 meters. At least two organism groupings were distinguishable, specifically:
a. Alvinella worm tentacle. Worm #19 was 7 cm in length, (sample #145).
b. Alvinella symbiont bacteria scraped off the mid-dorsal section (sample #142) of worm #19.
1. Messenger RNA (mRNA) was isolated from the environmental organisms using a mRNA isolation kit (Pharmacia).
2. mRNA was treated with methylmercury II hydroxide ($CH_3HgOH$) to relax secondary structure.
3. First strand cDNA was synthesized with random primers (9-mers from the PrimeIt II kit (Stratagene), dNTPs containing methyl-dCTP, $^{32}$P-dATP and MMLV-reverse transcriptase.
4. Second strand cDNA was synthesized with dNTPs with excess dCTP to dilute out the methyl-dCTP in the first strand reaction, RNase H and DNA polymerase I.
5. The double-stranded cDNA was blunted with cloned Pfu polymerase.
6. The blunted double-stranded cDNA was ligated to EcoR I adapters composed of 9- and 13-mer oligos which, when annealed, created an EcoR I cohesive end.
7. The ligated samples were phosphorylated with T4 polynucleotide kinase.
8. cDNA was size fractionated on a Sephacryl S-500 spin column.
9. Size fractionated cDNA was ligated to prepared Lambda ZAP® II arms (Stratagene).
10. The ligation reactions were packaged with Gigapack® III lambda packaging extract and titered on XL1-Blue MRF' host cells (Stratagene).

Example 9

Genomic Library Construction

1. Genomic DNA dissolved in TE buffer is vigorously passed through a 25 gauge double-hubbed needle until the sheared fragments are in the desired size range.
2. DNA ends are "polished" or blunted with Mung Bean nuclease.
3. EcoRI restriction sites in the target DNA are protected with EcoRI methylase.
4. EcoRI linkers [ggaattcc] are ligated to the blunted/protected DNA using a very high molar ratio of linkers to target DNA.
5. Linkers are cut back with EcoRI restriction endonuclease and the DNA is size fractionated using sucrose gradients.
6. Target DNA is ligated to the ZAPII vector, packaged using in vitro lambda packing extracts, and grown in the appropriate E. coli XLI Blue host cell.

Example 10

Library Screening

The following is a representative example of a procedure for screening an expression library prepared in accordance with Example 9.
The general procedures for testing for various chemical characteristics is generally applicable to substrates other than those specifically referred to in this Example.
Screening for Activity.
Plates of the library prepared as described in Example 6 are used to multiply inoculate a single plate containing 200 L of LB Amp/Meth, glycerol in each well. This step is performed using the High Density Replicating Tool (HDRT) of the Beckman Biomek with a 1% bleach, water, isopropanol, air-dry sterilization cycle between each inoculation. The single plate is grown for 2 h at 37 C and is then used to inoculate two white 96-well Dynatech microtiter daughter plates containing 250 L of LB Amp/Meth, glycerol in each well. The original single plate is incubated at 37 C for 18 h, then stored at -80 C. The two condensed daughter plates are incubated at 37 C also for 18 h. The condensed daughter plates are then heated at 70 C for 45 min. to kill the cells and inactivate the host E. coli enzymes. A stock solution of 5 mg/mL morphourea phenylalanyl-7-amino-4-trifluoromethyl coumarin (MuPheAFC, the 'substrate') in DMSO is diluted to 600 M with 50 mM pH 7.5 Hepes buffer containing 0.6 mg/mL of the detergent dodecyl maltoside.

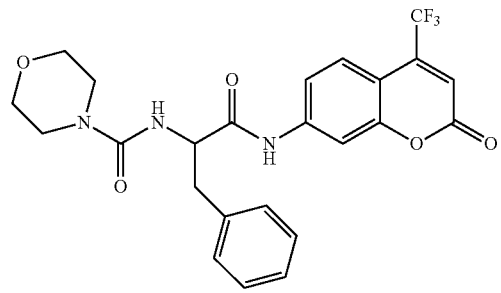

Mu-Phe-AFC

Fifty L of the 600 M MuPheAFC solution are added to each of the wells of the white condensed plates with one 100 L mix cycle using the Biomek to yield a final concentration of substrate of ~100 M. The fluorescence values are recorded (excitation=400 nm, emission=505 nm) on a plate reading fluorometer immediately after addition of the substrate (t=0). The plate is incubated at 70 C for 100 min, then allowed to cool to ambient temperature for 15 additional minutes. The fluorescence values are recorded again (t=100). The values at t=0 are subtracted from the values at t=100 to determine if an active clone is present.
The data will indicate whether one of the clones in a particular well is hydrolyzing the substrate. In order to determine the individual clone which carries the activity, the source library plates are thawed and the individual clones are used to singly inoculate a new plate containing LB Amp/Meth, glycerol. As above, the plate is incubated at 37 C to grow the cells, heated at 70 C to inactivate the host enzymes, and 50 L of 600 M MuPheAFC is added using the Biomek. Additionally three other substrates are tested. They are methyl umbelliferone heptanoate, the CBZ-arginine rhodamine derivative, and fluorescein-conjugated casein (~3.2 mol fluorescein per mol of casein).

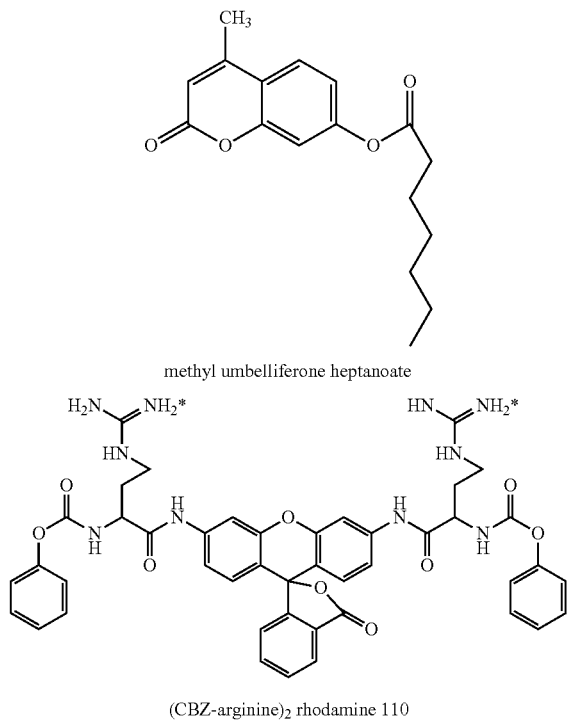

methyl umbelliferone heptanoate (CBZ-arginine)₂ rhodamine 110

The umbelliferone and rhodamine are added as 600 M stock solutions in 50 L of Hepes buffer. The fluorescein conjugated casein is also added in 50 L at a stock concentration of 20 and 200 mg/mL. After addition of the substrates the t=0 fluorescence values are recorded, the plate is incubated at 70 C, and the t=100 min. values are recorded as above.

These data indicate which plate the active clone is in, where the arginine rhodamine derivative is also turned over by this activity, but the lipase substrate, methyl umbelliferone heptanoate, and protein, fluorescein-conjugated casein, do not function as substrates.

Chiral amino esters may be determined using at least the following substrates:

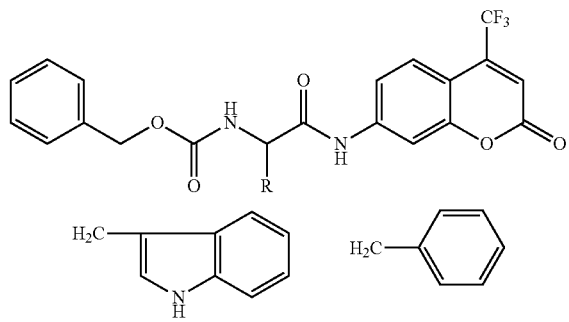

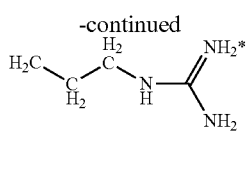

R = CH₃
   CH₂——OH
   CH₂——CO2*

For each substrate which is turned over the enantioselectivity value, E, is determined according to the equation below:

$$E = \frac{\ln[(1 - c(1 + ee_p)]}{\ln[(1 - c(1 - ee_p)]}$$

where $ee_p$=the enantiomeric excess (ee) of the hydrolyzed product and c=the percent conversion of the reaction. See Wong and Whitesides, Enzymes in Synthetic Organic Chemistry, 1994, Elsevier, Tarrytown, N.Y., pp. 9-12.

The enantiomeric excess is determined by either chiral high performance liquid chromatography (HPLC) or chiral capillary electrophoresis (CE). Assays are performed as follows: two hundred L of the appropriate buffer is added to each well of a 96-well white microtiter plate, followed by 50 L of partially or completely purified enzyme solution; 50 L of substrate is added and the increase in fluorescence monitored versus time until 50% of the substrate is consumed or the reaction stops, whichever comes first.

Example 11

Construction of a Stable, Large Insert Picoplankton Genomic DNA Library

Cell Collection and Preparation of DNA.

Agarose plugs containing concentrated picoplankton cells were prepared from samples collected on an oceanographic cruise from Newport, Oreg. to Honolulu, Hi. Seawater (30 liters) was collected in Niskin bottles, screened through 10 m Nitex, and concentrated by hollow fiber filtration (Amicon DC 10) through 30,000 MW cutoff polyfulfone filters. The concentrated bacterioplankton cells were collected on a 0.22 m, 47 mm Durapore filter, and resuspended in 1 ml of 2×STE buffer (1M NaCl, 0.1M EDTA, 10 mM Tris, pH 8.0) to a final density of approximately 1×10¹⁰ cells per ml. The cell suspension was mixed with one volume of 1% molten Seaplaque LMP agarose (FMC) cooled to 40 C, and then immediately drawn into a 1 ml syringe. The syringe was sealed with parafilm and placed on ice for 10 min. The cell-containing agarose plug was extruded into 10 ml of Lysis Buffer (10 mM Tris pH 8.0, 50 mM NaCl, 0.1M EDTA, 1% Sarkosyl, 0.2% sodium deoxycholate, 1 mg/ml lysozyme) and incubated at 37 C for one hour. The agarose plug was then transferred to 40 mls of ESP Buffer (1% Sarkosyl, 1 mg/ml proteinase K, in 0.5M EDTA), and incubated at 55 C for 16 hours. The solution was decanted and replaced with fresh ESP Buffer, and incubated at 55 C for an additional hour. The agarose plugs were then placed in 50 mM EDTA and stored at 4 C shipboard for the duration of the oceanographic cruise.

One slice of an agarose plug (72 l) prepared from a sample collected off the Oregon coast was dialyzed overnight at 4 C against 1 mL of buffer A (100 mM NaCl, 10 mM Bis Tris Propane-HCl, 100 g/ml acetylated BSA: pH 7.0@25 C) in a 2 mL microcentrifuge tube. The solution was replaced with 250 l of fresh buffer A containing 10 mM MgCl₂ and 1 mM DTT and incubated on a rocking platform for 1 hr at room temperature. The solution was then changed to 250 l of the same buffer containing 4U of Sau3A1 (NEB), equilibrated to 37 C in a water bath, and then incubated on a rocking platform in a 37 C incubator for 45 min. The plug was transferred to a 1.5 ml microcentrifuge tube and incubated at 68 C for 30 min to inactivate the enzyme and to melt the agarose. The agarose was digested and the DNA dephosphorylased using Gelase and HK-phosphatase (Epicentre), respectively, according to the manufacturer's recommendations. Protein was removed by gentle phenol/chloroform extraction and the DNA was ethanol precipitated, pelleted, and then washed with 70% ethanol. This partially digested DNA was resuspended in sterile $H_2O$ to a concentration of 2.5 ng/1 for ligation to the pFOS1 vector.

PCR amplification results from several of the agarose plugs (data not shown) indicated the presence of significant amounts of archaeal DNA. Quantitative hybridization experiments using rRNA extracted from one sample, collected at 200 m of depth off the Oregon Coast, indicated that planktonic archaea in this assemblage comprised approximately 4.7% of the total picoplankton biomass. This sample corresponds to "PACI"-200 m in Table 1 of DeLong et al. (DeLong, 1994), which is incorporated herein by reference. Results from archaeal-biased rDNA PCR amplification performed on agarose plug lysates confirmed the presence of relatively large amounts of archaeal DNA in this sample. Agarose plugs prepared from this picoplankton sample were chosen for subsequent fosmid library preparation. Each 1 ml agarose plug from this site contained approximately $7.5 \times 10^5$ cells, therefore approximately $5.4 \times 10^5$ cells were present in the 72 l slice used in the preparation of the partially digested DNA.

Vector arms were prepared from pFOS1 as described by Kim et al. (Kim, 1992). Briefly, the plasmid was completely digested with AstII, dephosphorylated with HK phosphatase, and then digested with BamHI to generate two arms, each of which contained a cos site in the proper orientation for cloning and packaging ligated DNA between 35-45 kbp. The partially digested picoplankton DNA was ligated overnight to the PFOS 1 arms in a 15 l ligation reaction containing 25 ng each of vector and insert and 1U of T4 DNA ligase (Boehringer-Mannheim). The ligated DNA in four microliters of this reaction was in vitro packaged using the Gigapack XL packaging system (Stratagene), the fosmid particles transfected to *E. coli* strain DH10B (BRL), and the cells spread onto $LB_{cm15}$ plates. The resultant fosmid clones were picked into 96-well microliter dishes containing $LB_{cm15}$ supplemented with 7% glycerol. Recombinant fosmids, each containing ca. 40 kb of picoplankton DNA insert, yielded a library of 3.552 fosmid clones, containing approximately $1.4 \times 10^8$ base pairs of cloned DNA. All of the clones examined contained inserts ranging from 38 to 42 kbp. This library was stored frozen at –80 C for later analysis.

Numerous modifications and variations of the present invention are possible in light of the above teachings; therefore, within the scope of the claims, the invention may be practiced other than as particularly described.

LITERATURE CITED

Amann R I, Ludwig W, Schleifer K H: Phylogenetic identification and in situ detection of individual microbial cells without cultivation. *Microbiological Reviews* 59(1):143-169, 1995.

Balows A, Trüper H G, Dworkin M, Harder W, Schleifer K-H (All eds): The Prokaryotes. $2^{nd}$ Ed. A Handbook on the Biology of bacteria: Ecophysiology, Isolation, Identification, Applications. ©1992. Springer-Verlag, New York.

Barnes W M: PCR amplification of up to 35-kb DNA with high fidelity and high yield from lambda bacteriophage templates. *Proceedings of the National Academy of Sciences, USA* 91(6):2216-2220, 1994.

Barns S M, Fundyga R E, Jeffries M W, Pace N R: Remarkable archaeal diversity detected in a Yellowstone National Park hot spring environment. *Proceedings of the National Academy of Sciences, USA* 91(5):1609-1613, 1994.

Berg J D, Fiksdal L: Rapid detection of total and fecal coliforms in water by enzymatic hydrolysis of 4-methylumbelliferone-beta-D-galactoside. *Appl Environ Microbiol* 54(8):2118-2122, (August) 1988.

Blackburn, C W: Rapid and alternative methods for the detection of salmonellas in foods. *J Appl Bacteriol* 75(3):199-214, 1993.

Cheng S, Fockler C, Barnes W M, Higuchi R: Effective amplification of long targets from cloned inserts and human genomic DNA. *Proceedings of the National Academy of Sciences, USA* 91(12):5695-5699, 1994.

Davey H M, Kell D B: Flow cytometry and cell sorting of heterogeneous microbial populations: the importance of single-cell analyses. *Microbiological Reviews* 60(4):641-696, 1996.

DeLong E F: Archaea in coastal marine environments. *Proceedings of the National Academy of Science USA* 89(12):5685-5689, 1992.

DeLong E F, Wu K Y, Prezelin B B, Jovine R V: High abundance of Archaea in Antarctic marine picoplankton. *Nature* 371(6499):695-697, 1994.

Desmonts C, Minet J, Colwell R, Cormier M: Fluorescent antibody method useful for detecting viable but non-culturable *Salmonella* ssp. in chlorinated waste-water. *Appl Environ Microbiol* 56(5):1448-52, 1990.

Edberg S C, Gam K, Bottenbley C J, Singer J M: Rapid spot test for the determination of esculin hydrolysis. *J Clinical Microbiology* 4(2):180-184, 1976.

Galbraith D W: Flow cytometry and sorting of plant protoplasts and cells. *Methods Cell Biol* 42(Pt B):539-61, 1994.

Gerhardt P, Murray R G E, Wood W A, Krieg N R (All eds): Methods for General and Molecular Bacteriology. American Society for Microbiology, Washington, D.C. ©1994.

Giovannoni S J, Britschgi T B, Moyer C L, Field K G: Genetic diversity in Sargasso Sea bacterioplankton. *Nature* 345 (6270):60-63, 1990.

Haukanes B I, Kvam C: Application of magnetic beads in bioassays. *Biotechnology (NY)* 11(1):60-63, 1993.

Holben W E: Methods of Soil Analysis, Part 2, Microbiological and Biochemical Properties 727-751. (Editorial committee, R. W. Weaver, chair). Series: Soil Science Society of America Book Series, No. 5. Soil Science Society of America. Madison, Wis., ©1994.

Holben W E, Harris D: DNA-based monitoring of total bacterial community structure in environmental samples. *Molecular Ecology* 4(5):627-631, 1995.

International Union of Biochemistry and Molecular Biology, Nomenclature Committee: Enzyme nomenclature 1992: recommendations of the Nomenclature Committee of the International Union of Biochemistry and Molecular Biology on the nomenclature and classification of enzymes/prepared for NC-IUBMB by Edwin C. Webb. Academic Press, c1992.

Jansson J K, Prosser J I: Quantification of the presence and activity of specific microorganisms in nature. *Mol Biotechnol* 7(2):103-120, 1997.

Kachel V, Messerschmidt R, Hummel P: Eight-parameter PC-AT based flow cytometric data system. *Cytometry* 11(7):805-812, 1990.

Kim U J, Shizuya H, de Jong P J, Birren B, Simon M I: Stable propagation of cosmid sized human DNA inserts in an F factor based vector *Nucleic Acids Res* 20(5):1083-1085, 1992.

Ko M S: An 'equalized cDNA library' by the reassociation of short double-stranded cDNAs. *Nucleic Acids Research* 18(19):5705-5711, 1990.

Ko M S, Ko S B, Takahashi N, Nishiguchi K, Abe K: Unbiased amplification of a highly complex mixture of DNA fragments by 'lone linker'-tagged PCR. *Nucleic Acids Research* 18(14):4293-4294, 1990.

Laplace-Builhe C, Hahne K, Hunger W, Tirilly Y, Drocourt J L: Application of flow cytometry to rapid microbial analysis in food and drink industries. *Biol Cell* 78(1-2):123-128, 1993.

Lederberg J (ed in chief): Encyclopedia of Microbiology Vol. 1-4. ©1992. Academic Press, Inc., San Diego.

Loessner M J, Schneider A, Scherer S: A new procedure for efficient recovery of DNA, RNA, and proteins from *Listeria* cells by rapid lysis with a recombinant bacteriophage endolysin. *Appl Environ Microbiol* 61(3):1150-1152, 1995.

Manuelidis L: A simplified method for preparation of mouse satellite DNA. *Analytical Biochemistry* 78(2):561-568, 1977.

Marquet-Van der Mee N, Audurier A: Proposals for optimization of the international phage typing system for *Listeria monocytogenes*: combined analysis of phage lytic spectrum and variability of typing results. *Appl Environ Microbiol* 61(1):303-309, 1995.

Muller W, Gautier F: Interactions of heteroaromatic compounds with nucleic acids. A-T-specific non-intercalating DNA ligands. *European Journal of Biochemistry* 54(2):385-394, 1975.

Norris D A, Ryan S B, Kissinger R M, Fritz K A, Boyce S T: Systematic comparison of antibody-mediated mechanisms of keratinocyte lysis in vitro. *J Immunol* 135(2):1073-1079, 1985.

Osawa T: The separation of immunocyte subpopulations by use of various lectins. *Adv Exp Med Biol* 228:83-104, 1988.

Porter J, Deere D, Pickup R, Edwards C: Fluorescent probes and flow cytometry: new insights into environmental bacteriology. *Cytometry* 23(2):91-96, (Feb. 1)1996.

Porter J, Edwards C, Morgan J A, Pickup R W: Rapid, automated separation of specific bacteria from lake water and sewage by flow cytometry and cell sorting. *Appl Environ Microbiol* 59(10):3327-33, 1993.

Porter J, Pickup R, Edwards C: Flow cytometric detection of specific genes in genetically modified bacteria using in situ polymerase chain reaction. *FEMS Microbiol Lett* 134(1):51-56, 1995.

Prusiner S B: Biology and genetics of prion diseases. *Annu Rev Microbiol* 48:655-686, 1994.

Reysenbach A L, Giver L J, Wickham G S, Pace N R: Differential amplification of rRNA genes by polymerase chain reaction. *Appl Environ Microbiol* 58(10):3417-3418, 1992.

Rickwood D, Ford T, Graham J: Nycodenz: a new nonionic iodinated gradient medium. *Anal Biochem* 123(1):23-31, 1982.

Saiki R K, Gelfand D H, Stoffel S, Scharf S J, Higuchi R, Horn G T, Mullis K B, Erlich H A: Primer-directed enzymatic amplification of DNA with a thermostable DNA polymerase. *Science* 239(4839):487-491, 1988.

Sambrook J, Fritsch E F, Maniatis T: Molecular Cloning. A Laboratory Manual, Cold Spring Habor Press, Cold Spring Habor, N.Y., c1989.

Sarkis G J, Jacobs W R Jr., Hatfull G F: L5 luciferase reporter mycobacteriophages: a sensitive tool for the detection and assay of live mycobacteria. *Mol Microbiol* 15(6):1055-1067, 1995.

Takahashi N, Ko M S: Toward a whole cDNA catalog: construction of an equalized cDNA library from mouse embryos. *Genomics* 23(1):202-210, 1994.

Trevors J T, van Elsas D D: Nucleic Acids in the Environment Methods & Applications. Springer Laboratory, 1995.

Torsvik V, Goksoyr J, Daae F L: High diversity in DNA of soil bacteria. *Applied and Environmental Microbiology* 56(3):782-787, 1990.

Torsvik V, Salte K, Sorheim R, Goksoyr J: Comparison of phenotypic diversity and DNA heterogeneity in a population of soil bacteria. *Applied and Environmental Microbiology* 56(3):776-781, 1990.

Troussellier M, Courties C, Vaguer A: Recent applications of flow cytometry in aquatic microbial ecology. Biol Cell 78(1-2):111-121, 1993.

Ward D M, Weller R, Bateson M M: 16S rRNA sequences reveal numerous uncultured microorganisms in a natural community. *Nature* 345(6270):63-65, 1990.

Weissman S M: Molecular genetic techniques for mapping the human genome. *Mol Biol Med* 4(3):133-143, 1987.

U.S. Pat. No. 4,591,554; May 27, 1986 (Filed Sep. 16, 1983). Koumura I, Kanou H, Okunishi M, Yamada K: Rapid method for detecting microorganisms.

U.S. Pat. No. 4,689,295; Aug. 25, 1987 (Filed Sep. 2, 1983). Taber R L, Fitts R A: Test for *Salmonella*.

U.S. Pat. No. 4,784,943; Nov. 15, 1988 (Filed May 22, 1987). Warren G J, Wolber P K: Ice nucleation immunoassay.

U.S. Pat. No. 4,874,695; Oct. 17, 1989 (Filed Feb. 21, 1985). Pincus D H: Rapid identification of yeast and other fungal microorganisms by enzyme detection.

U.S. Pat. No. 5,096,668; Mar. 17, 1992 (Filed Apr. 26, 1990). Thompson T E: Diagnostic test slide.

U.S. Pat. No. 5,422,242; Jun. 6, 1995 (Filed Jul. 17, 1992). Young K: *Mycobacterium* primers and probes.

U.S. Pat. No. 5,429,933; Jul. 4, 1995 (Filed Oct. 14, 1994). Edberg S C: Detection of first generation environmental sourced microbes in an environmentally-derived sample.

E.P.N. 0 428 000 A1; May 22, 1991 (Filed Oct. 29, 1990). Krafft G A: Fluorogenic substrates for the detection of proteolytic enzyme activity.

I.P.N. WO 95/11986; May 4, 1995 (Filed Oct. 24, 1994). Fisher P B, Jiang H: Method for generating a subtracted cDNA library and uses of the generated library.

I.P.N. WO 95/08647; Mar. 30, 1995 (Filed Sep. 23, 1994). Soares M B, Efstratiadis A: Method for construction of normalized cDNA libraries.

TABLE 1

| A2 |
|---|
| Fluorescein conjugated casein (3.2 mol fluorescein/mol casein) |
| CBZ-Ala-AMC |
| t-BOC-Ala-Ala-Asp-AMC |
| succinyl-Ala-Gly-Leu-AMC |
| CBZ-Arg-AMC |
| CBZ-Met-AMC |
| morphourea-Phe-AMC |
| (t-BOC = t-butoxy carbonyl, CBZ = carbonyl benzyloxy. |
| AMC = 7-amino-4-methyl coumarin |

TABLE 1-continued

AA3

[Structures: alanine amide and phenylalanine amide]

AB3

[Structures: two hydantoin derivatives]

AC3

[Structures: N-acetyl alanine and N-acetyl phenylalanine]

AD3

Fluorescein conjugated casein
t-BOC- Ala-Ala-Asp-AFC
CBZ- Ala-Ala-Lys-AFC
succinyl-Ala-Ala-Phe-AFC
succinyl-Ala-Gly-Leu-AFC
AFC = 7-amino-4-trifluoromethyl coumarin.)

AE3

Fluorescein conjugated
casein

AF3 t-BOC-Ala-Ala-Asp-AFC
CBZ-Asp-AFC

AG3

CBZ- Ala-Ala-Lys-AFC
CBZ-Arg-AFC

AH3 succinyl-Ala-Ala-Phe-AFC
CBZ-Phe-AFC
CBZ-Trp-AFC

AI3 succinyl-Ala-Gly-Leu-AFC
CBZ-Ala-AFC
CBZ-Sewr-AFC

TABLE 2

L2

[Structures: four 4-methylcoumarin ester derivatives with varying acyl chain lengths]

TABLE 2-continued
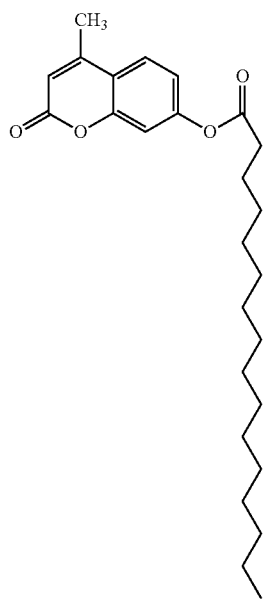 [SMILES: CCCCCCCCCCCCCCCC(=O)Oc1ccc2c(C)cc(=O)oc2c1]
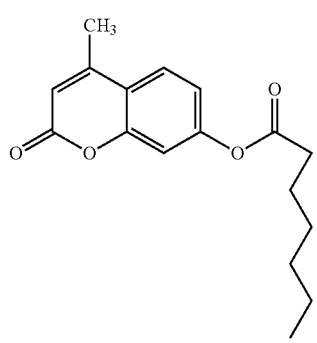 [SMILES: CCCCCCC(=O)Oc1ccc2c(C)cc(=O)oc2c1]
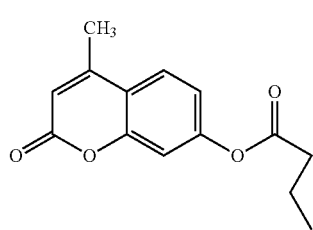 [SMILES: CCCC(=O)Oc1ccc2c(C)cc(=O)oc2c1]
TABLE 2-continued
LA3
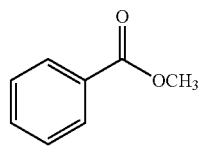
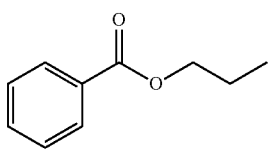
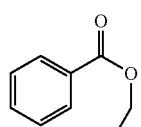

TABLE 2-continued
LB3
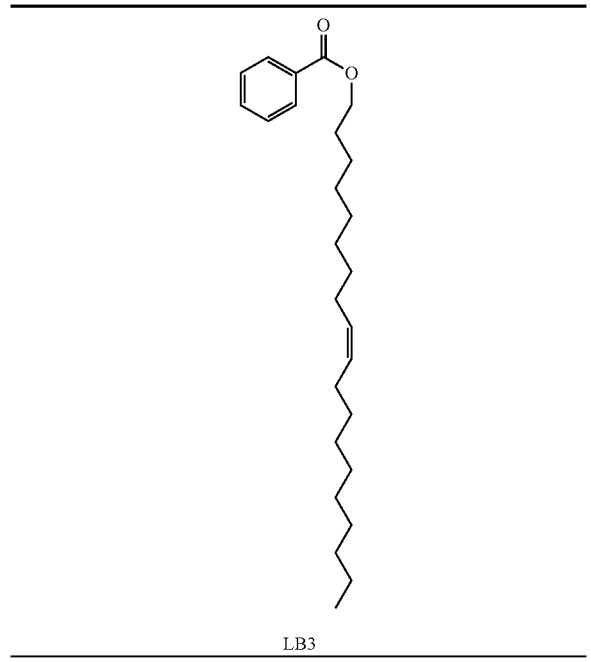
LC3
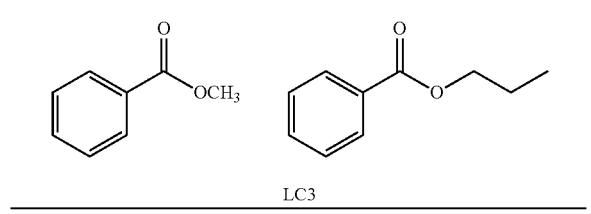
LD3
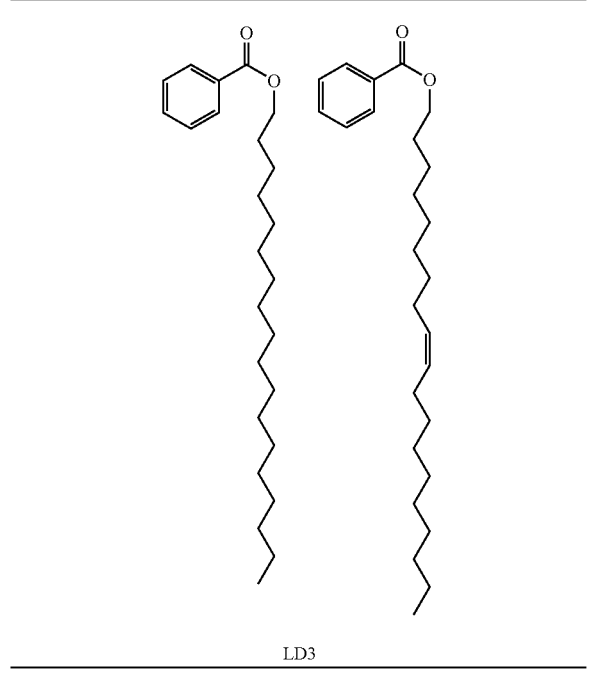
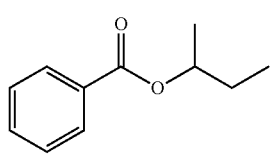
TABLE 2-continued
LE3
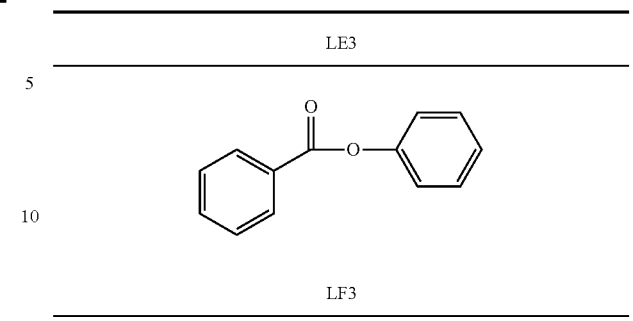
LF3
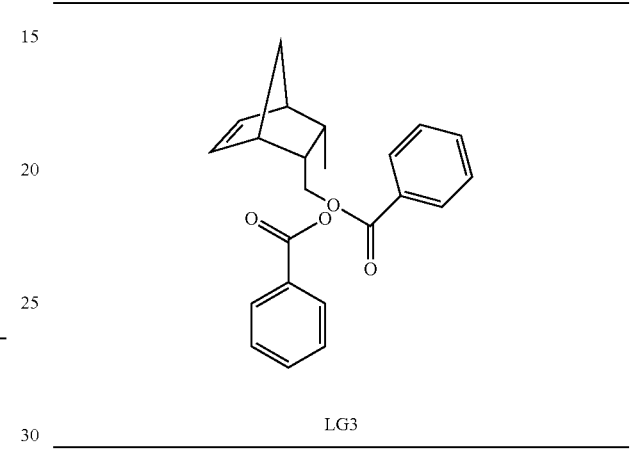
LG3
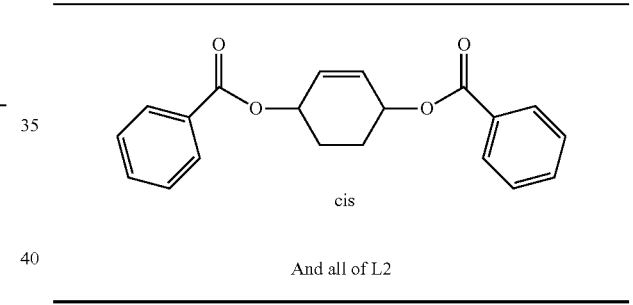
cis
And all of L2
TABLE 3
LH3
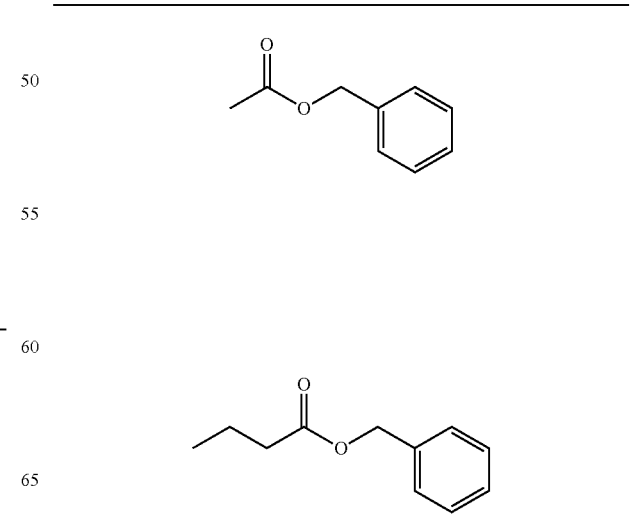

TABLE 3-continued
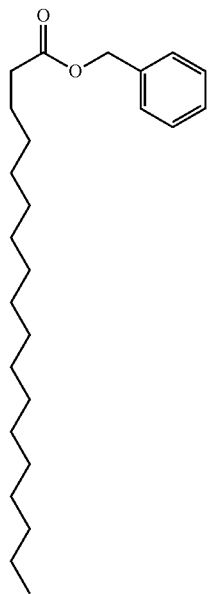 [SMILES: CCCCCCCCCCCCCCCCCC(=O)OCc1ccccc1]
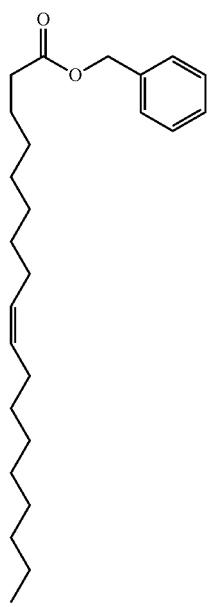 [SMILES: CCCCCCCC/C=C\CCCCCCCC(=O)OCc1ccccc1]
LI3
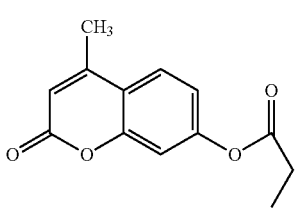 [SMILES: CCC(=O)Oc1ccc2c(C)cc(=O)oc2c1]
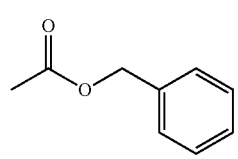
TABLE 3-continued
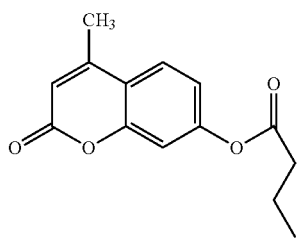 [SMILES: CCCC(=O)Oc1ccc2c(C)cc(=O)oc2c1]
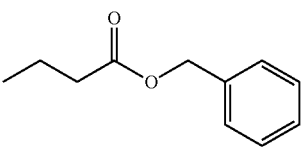
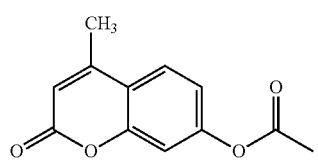 [SMILES: CC(=O)Oc1ccc2c(C)cc(=O)oc2c1]
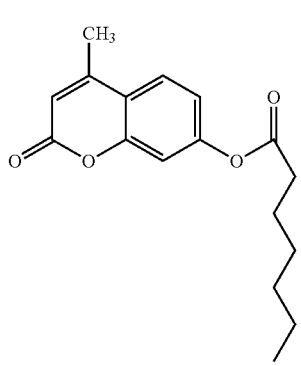 [SMILES: CCCCCCC(=O)Oc1ccc2c(C)cc(=O)oc2c1]
LJ3
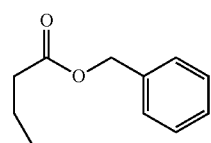

TABLE 3-continued
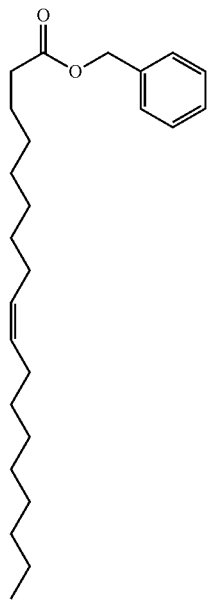 [SMILES: CCCCCCCC/C=C\CCCCCCCC(=O)OCc1ccccc1]
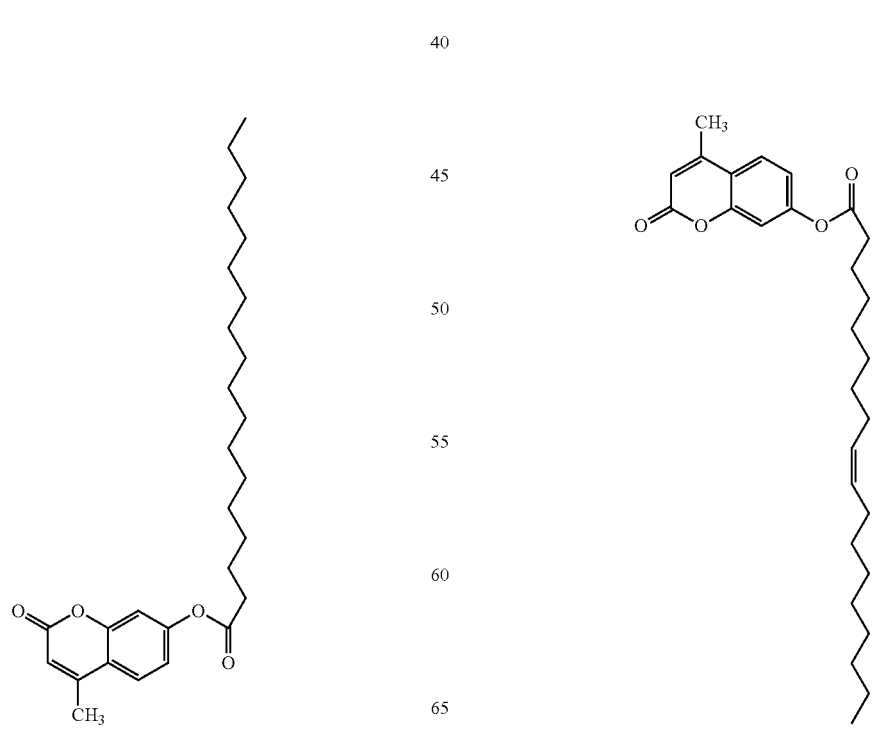

TABLE 3-continued

LK3

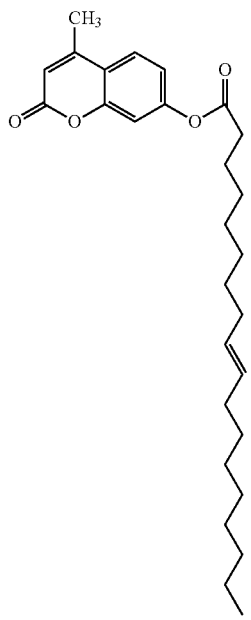 [SMILES: CCCCCCCC/C=C/CCCCCCCC(=O)Oc1ccc2c(C)cc(=O)oc2c1]

LL3

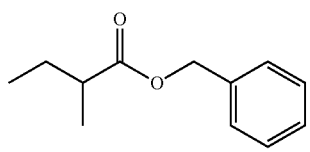

LM3

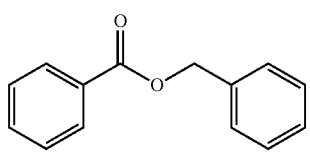 [SMILES: O=C(OCc1ccccc1)c1ccccc1]

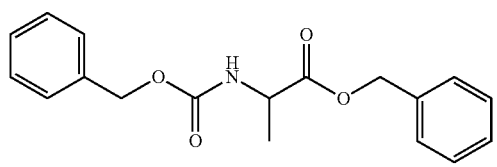

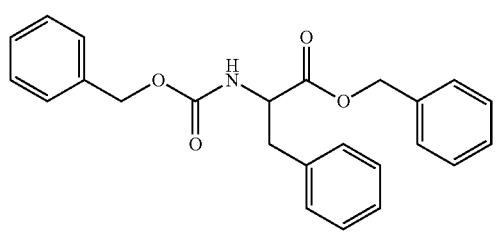

TABLE 3-continued

LN3

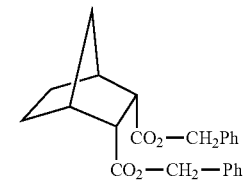

LO3

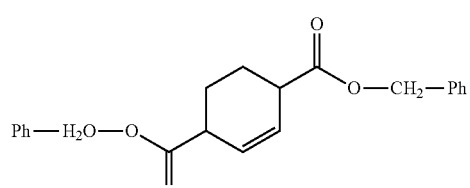

cis

TABLE 4

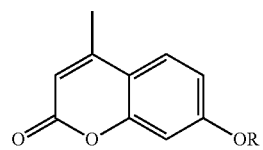

4-methyl umbelliferone
wherein R =

| | |
|---|---|
| G2 | β-D-galactose |
| | β-D-glucose |
| | β-D-glucuronide |
| GB3 | β-D-cellotrioside |
| | β-B-cellobiopyranoside |
| GC3 | β-D-galactose |
| | α-D-galactose |
| GD3 | β-D-glucose |
| | α-D-glucose |
| GE3 | β-D-glucuronide |
| GI3 | β-D-N,N-diacetylchitobiose |
| GJ3 | β-D-fucose |
| | α-L-fucose |
| | β-L-fucose |
| GK3 | β-D-mannose |
| | α-D-mannose |
| | non-Umbelliferyl substrates |
| GA3 | amylose [polyglucan α1,4 linkages], amylopectin [polyglucan branching α1,6 linkages] |
| GF3 | xylan [poly 1,4-D-xylan] |
| GG3 | amylopectin, pullulan |
| GH3 | sucrose, fructofuranoside |

What is claimed is:

1. A method for forming a catalogued nucleic acid library from an initial organism sample comprised of heterogeneous organisms, said method comprising:
   (a) forming a derived organism sample from the initial heterogeneous organism sample by subjecting all or a part of said initial heterogeneous organism sample to a method of selection, such that proportional representations of the constituents in said derived organism sample are adjusted by subjecting all or a part of said initial heterogeneous organism sample to a method of positive and/or negative selection for at least one organism marker which is a nucleic acid marker characteristic of an organism in the initial organism sample;
   (b) isolating an initial nucleic acid sample from said derived organism sample of step (a);
   (c) forming a derived nucleic acid library from said isolated initial nucleic acid sample of step (b), such that the proportional representations of the constituents in said derived nucleic acid library are adjusted to advantage by performing the following steps in any order, and at least one time:
      (i) subjecting all or a part of said initial nucleic acid sample to a period of selection,
      (ii) recovering a fraction of said initial nucleic acid sample having at least one desired characteristic, and
      (iii) assembling all or a part of said derived nucleic acid sample into a nucleic acid library;
   thereby forming a catalogued nucleic acid library from the initial organism sample comprised of heterogeneous organisms.

2. A method for forming a catalogued nucleic acid library from an initial organism sample comprised of heterogeneous organisms, said method comprising:
   (a) forming a derived organism sample from the initial heterogeneous organism sample, such that proportional representations of the constituents in said derived organism sample are adjusted to advantage by recovering a fraction of said initial heterogeneous organism sample having at least one organism marker which is a nucleic acid marker characteristic of an organism in the initial organism sample;
   (b) isolating an initial nucleic acid sample from said derived organism sample; and
   (c) forming a derived nucleic acid library from said isolated initial nucleic acid sample of step (b), such that the proportional representations of the constituents in said derived nucleic acid library are adjusted to advantage by performing the following steps in any order, and at least one time:
(i) subjecting all or a part of said initial nucleic acid sample to a period of selection,
(ii) recovering a fraction of said initial nucleic acid sample having at least one desired characteristic, and
(iii) assembling all or a part of said derived nucleic acid sample into a nucleic acid library;
thereby forming a catalogued nucleic acid library from the initial heterogeneous organism sample comprised of heterogeneous organisms.

3. A method for forming a catalogued nucleic acid library from an initial organism sample comprised of heterogeneous organisms, said method comprising:
(a) forming a derived organism sample from the initial heterogeneous organism sample, such that proportional representations of the constituents in said derived organism sample are adjusted to advantage by performing in any order both (i) subjecting all or a part of said initial heterogeneous organism sample to a method of positive and/or negative selection for at least one organism marker which is a nucleic acid marker characteristic of an organism in the initial organism sample, and (ii) recovering a fraction of said initial heterogeneous organism sample having at least one desired characteristic;
(b) isolating an initial nucleic acid sample from said derived organism sample; and
(c) forming a derived nucleic acid library from said isolated initial nucleic acid sample of step (b), such that the proportional representations of the constituents in said derived nucleic acid library are adjusted to advantage by performing the following steps in any order, and at least one time:
(i) subjecting all or a part of said initial nucleic acid sample to a period of selection,
(ii) recovering a fraction of said initial nucleic acid sample having at least one desired characteristic, and
(iii) assembling all or a part of said derived nucleic acid sample into a nucleic acid library;
thereby forming a catalogued nucleic acid library from the initial heterogeneous organism sample comprised of heterogeneous organisms.

4. The method of claim 1 wherein the subjecting all or a part of said initial heterogeneous organism sample to a method of selection of step (a) further comprises: (i) resolving heterogeneity of the initial heterogeneous organism sample according to at least one organism marker such that the initial organism sample is normalized with respect to organisms exhibiting the at least one common organism marker before the subjecting all or a part of said initial organism sample to a method of selection; or (ii) resolving heterogeneity of the organism sample after the selection step of (a) but before step (b) by normalizing the initial organism sample with respect to organisms exhibiting the at least one common organism marker.

5. The method of claim 4 wherein the at least one organism marker comprises a 16S rRNA content.

6. The method of claim 1 wherein the subjecting all or a part of said initial heterogeneous organism sample to a method of selection of step (a) comprises selecting said initial heterogeneous organism sample using at least one organism marker such that the derived organism sample is selectively enriched with respect to organisms exhibiting the selected at least one organism marker.

7. The method of claim 6 wherein the selected organisms in the derived organism sample exhibit increased 16S rRNA content or 18S rRNA content compared to those in the unselected initial organism sample.

8. The method of claim 4 wherein step (a) further comprises initially resolving heterogeneity of said initial heterogeneous organism sample according to at least two organism markers.

9. The method of claim 1 wherein step (c) comprises resolving heterogeneity of said initial nucleic acid sample according to at least one nucleic acid marker such that the derived nucleic acid library is normalized with respect to the nucleic acids exhibiting the at least one organism marker.

10. The method of claim 9 wherein the at least one nucleic acid marker is G+C content of the nucleic acids in the derived nucleic acid library.

11. The method of claim 1 wherein step (c) further comprises resolving heterogeneity of the initial nucleic acid sample according to at least one nucleic acid marker such that the derived nucleic acid library is selectively enriched with respect to nucleic acids exhibiting the at least one nucleic acid marker.

12. The method of claim 11 wherein the at least one nucleic acid marker is G+C content of the nucleic acids in the derived nucleic acid library.

13. The method of claim 1 wherein step (c) further comprises resolving heterogeneity of said initial nucleic acid sample according to at least two nucleic acid markers such that the derived nucleic acid library is advantageously adjusted with respect to nucleic acids exhibiting each of said nucleic acid markers.

14. The method of claim 1 wherein step (c) comprises resolving heterogeneity of the initial nucleic acid sample according to at least one nucleic acid marker such that the derived nucleic acid library is normalized with respect to nucleic acids exhibiting the at least one nucleic acid marker.

15. The method of claim 1 wherein the at least one organism marker comprises 18S rRNA.

16. The method of claim 1 wherein the at least one organism marker comprises G+C content of the nucleic acids in the derived nucleic acid library.

17. The method of claim 1 wherein step (c) comprises resolving heterogeneity of the initial nucleic acid sample according to at least one nucleic acid marker such that the derived nucleic acid library is selectively enriched with respect to nucleic acids that exhibit the at least one nucleic acid marker.

18. The method of claim 1 wherein the at least one organism marker comprises 16S rRNA content or 18S rRNA content.

19. The method of claim 1 wherein the at least one nucleic acid marker comprises G+C content of the nucleic acids in the derived nucleic acid library.

20. The method of claim 2 wherein step (c) comprises resolving heterogeneity of said initial nucleic acid sample according to at least two nucleic acid markers such that the derived nucleic acid library is advantageously adjusted with respect to nucleic acids exhibiting each of said at least two nucleic acid markers.

21. The method of claim 2 wherein step (c) comprises resolving heterogeneity of said initial nucleic acid sample according to at least one nucleic acid marker such that the derived nucleic acid library is normalized with respect to nucleic acids that exhibit the at least one nucleic acid marker.

22. The method of claim 2 wherein step (c) comprises resolving heterogeneity of said initial nucleic acid sample according to at least one nucleic acid marker such that the derived nucleic acid library is selectively enriched with respect to nucleic acids that exhibit the at least one nucleic acid marker.

23. The method of claim 22 wherein the at least one organism marker comprises 16S rRNA content or 18S rRNA content.

24. The method of claim 22 wherein the at least one nucleic acid marker comprises G+C content of nucleic acids.

25. The method of claim 3 wherein step (c) comprises resolving heterogeneity of said initial nucleic acid sample according to at least two nucleic acid markers such that the derived nucleic acid library is advantageously adjusted with respect to nucleic acids that exhibit each of said at least two nucleic acid markers.

26. The method of claim 25 wherein the at least one organism marker comprises 16S rRNA content or 18S rRNA content.

27. The method of claim 3 wherein step (c) comprises resolving heterogeneity of said initial nucleic acid sample according to at least one nucleic acid marker such that the derived nucleic acid library is normalized with respect to nucleic acids that exhibit that at least one nucleic acid marker.

28. The method of claim 27 wherein the at least one nucleic acid marker comprises the G+C content of nucleic acids.

29. The method of claim 3 wherein step (c) comprises resolving heterogeneity of said initial nucleic acid sample according to at least one nucleic acid marker such that the derived nucleic acid library is selectively enriched with respect to nucleic acids that exhibit the at least one nucleic acid marker.

30. The method of claim 29 wherein the at least one nucleic acid marker comprises G+C content of the nucleic acids in the derived nucleic acid library.

31. The method of claim 2 wherein step (c) further comprises forming a genomic DNA library, thereby forming a catalogued genomic DNA library.

32. The method of claim 1 wherein step (c) further comprises forming a genomic gene cluster DNA library, thereby forming a catalogued genomic gene cluster DNA library.

33. The method of claim 1, wherein step (c) comprises forming a cDNA library, thereby forming a catalogued cDNA library.

34. The method of claim 1 wherein step (a) further comprises forming a derived organism sample that consists essentially of environmental organisms.

35. The method of claim 2 wherein step (a) comprises forming a derived organism sample that consists essentially of environmental organisms.

36. The method of claim 3 wherein step (a) further comprises forming a derived organism sample that consists essentially of environmental organisms.

37. The method of claim 1 wherein the initial organism sample is a direct environmental sample.

38. The method of claim 2 wherein the initial organism sample is a direct environmental sample.

39. The method of claim 3 wherein the initial organism sample is a direct environmental sample.

40. The method of claim 1 wherein the nucleic acid marker is a nucleic acid sequence.

41. The method of claim 2 wherein the nucleic acid marker is a nucleic acid sequence.

42. The method of claim 3 wherein the nucleic acid marker is a nucleic acid sequence.

43. The method of claim 1 wherein the nucleic acid marker is an expressed protein product of a nucleic acid.

44. The method of claim 2 wherein the nucleic acid marker is an expressed protein product of a nucleic acid.

45. The method of claim 3 wherein the nucleic acid marker is an expressed protein product of a nucleic acid.

46. The method of claim 1 wherein the nucleic acid marker is a biochemical process related to an expressed protein product of a nucleic acid.

47. The method of claim 2 wherein the nucleic acid marker is a biochemical process related to an expressed protein product of a nucleic acid.

48. The method of claim 3 wherein the nucleic acid marker is a biochemical process related to an expressed protein product of a nucleic acid.

* * * * *